United States Patent [19]

Molin et al.

[11] Patent Number: 5,545,541
[45] Date of Patent: Aug. 13, 1996

[54] STABILIZATION OF UNSTABLY INHERITED REPLICONS

[75] Inventors: Søren Molin, Holte; Kenn A. Gerdes, Virum; Poul B. Rasmussen; Poul K. Andersson, both of Copenhagen, all of Denmark

[73] Assignee: Benzon Pharma A/S, Hvidovre, Denmark

[21] Appl. No.: 406,880

[22] Filed: Sep. 13, 1989

Related U.S. Application Data

[63] Continuation of Ser. No. 29,760, Feb. 13, 1987, abandoned, which is a continuation of PCT/DK86/00070, Jun. 18, 1986.

[30] Foreign Application Priority Data

Jun. 18, 1985 [DK] Denmark ................... 2756/85

[51] Int. Cl.⁶ .................... C12N 15/68; C12N 15/69; C12N 15/74
[52] U.S. Cl. ............ 435/172.3; 435/691; 435/252.3; 435/320.1; 435/880; 435/874; 935/42; 935/44; 935/45; 935/46
[58] Field of Search ................ 435/172.3, 320, 435/69.1, 91, 252.3, 880, 874; 935/42, 44, 45, 46

[56] References Cited

U.S. PATENT DOCUMENTS

| 4,760,022 | 7/1988 | Molin et al. ................ 435/320.1 |
| 4,806,471 | 2/1989 | Molin et al. ................ 435/68 |

FOREIGN PATENT DOCUMENTS

| 49619 | 10/1981 | European Pat. Off. . |
| 080848 | 11/1982 | European Pat. Off. . |
| 95947 | 6/1983 | European Pat. Off. . |
| 106542 | 9/1983 | European Pat. Off. . |

OTHER PUBLICATIONS

Ray et al. 1984. Plasmid 11: 272–275. (May 1984).
Chang et al. 1978. J of Bacti 134: 1141–1156.
Loh et al. 1986 (Nov.) FEMS Microbiology Letters 37: 179–182.
Loh et al. 1988. Gene 66: 259–268.
Gerdes et al. 1986. (Aug.) EMBO J. 5: 2023–2029.
Gerdes et al. 1988 J. Mol. Biol. 203: 119–130.
ATCC Bacteria Catalogue, 1985. #29055 on p. 72.
Ogura et al.: Proc. Natl. Acad. Sci. USA, 80, 1983, pp. 4784–4788.
Bech et al.: The EMBO Journal 4(4), 1985, pp. 1059–1066.
Gerdes et al.: J. Bacteriol. 161(1), 1985, pp. 292–298.
Prentki et al.: Gene 17, 1982, pp. 189–196.
Light et al.: The EMBO Journal 2(1), 1983, pp. 93–98.
Simmons and Kleckner: Cell 34, 1983, pp. 683–691.
Mizuno et al.: Proc. Natl. Acad. Sci. USA, 81, 1984, pp. 1966–1970.
Izant et al.: Cell 36, 1984, pp. 1007–1015.
Poulsen et al., "A family of genes encoding a cell–killing function may be conserved in all Gram–negative bacteria", Molecular Microbiology (1989) 3 (11), 1463–1472.
Light et al., "The Sites of Action of the two Copy Number Control Functions of Plasmid R1", Mol. Gen. Genet. (1982) 187 : 486, 493.
Bagdasarian et al., Gene. 16 (1981) 237–247.
Meacock, P. A.; Cohen, S. N. Partitioning of Bacterial Plasmids during cell division: a cis–acting locus that accomplishes stable plasmid inheritance, cell(20) 2 543–53 (1980).

*Primary Examiner*—Patricia R. Moody
*Assistant Examiner*—B. White
*Attorney, Agent, or Firm*—Iver P. Cooper

[57] ABSTRACT

The stable maintenance of a replicon in a population of growing cells is ensured by providing the replicon with a sequence which encodes a product capable of killing the cell harboring the replicon or the progeny of the cell (or encodes a precursor for the product) and a sequence encoding an antagonist for the killing product (or a precursor for the antagonist). The antagonist is one which suppresses the killing product (or a precursor for the killing product) in cells harboring the replicon, whereas the antagonist activity decays when the replicon is lost from the cell so that the antagonist (or its precursor) is no longer continuously expressed. This means that the killing product (or its precursor) present in the now replicon-free cell is no longer suppressed by the antagonist, resulting in cell death.

Cells containing the thus stabilized replicon may be grown on a large scale without any significant loss of the replicon from the cell population even when no selection pressure is applied.

14 Claims, 19 Drawing Sheets

```
1
  AACAAACTCCGGGAGGCAGCCGTGATGCGGCAACAATCACACGGATTTCCCGTGAACGTCTGAATGAGCGGATTATTTCAGGGAAAGTGAGTGTGGTCA
  TTGTTTGAGGCCCTCCGTCGGCACTACGCGCCGTTGTTAGTGTGCCAGACTTACTCGCCAGACTTGCCAGACTTGCCCTAATAAAGTCCCTTTCACTCACACCAGT
                                                                    Ter

101
  GCGTGCAGGTATATGGGCTATGATGTGCCCGGCCTTGAGGCTTTCTGCCTCATGACCTGAAGCGTGGTTCTGTCTGCAGAAAGAAGATA
  CGCACGTCCATATACCCGATACTACACGGGCCGGAACTCCGAAAGACGGAGTACTGGACTTCCACCAAACAACGGCGCAACACCGTCTTTCTTCTAT
       phok    -10

201
  GCCCCGTAGTAAGTTAATTTCATTAACCACCACGAGGCATCCCTATGTCTAGTCCACATCAGGATAGCCTCTTACGCGCCTTTGCGCAAGGAGAAGAAG
  CGGGGCATCATTCAATTAAAAGTAATTGGTGGTGCTCCGTAGGATACAGATCAGTGTAGTCCTATCGGAGAATGGCGCGAAACGCGTTCCTCCTCTTC
            I                      II          fMet    -10             psok   -35
                                   fMet
```

Fig. 3a

```
301  fMet
     GCCATGAAACTACCACGAAGTTCCCTTGTCTGTTGATCGTGTCTCACACTGTTGATCGTGTCTGTGTTGATCTGTCACACTGTTGATATTCACTTATCTGACACGAAAATCGCTGTGCCAGA
     CGGTACTTTGATGGTGCTGCTTCAAGGGACAGACCACACACAGACCACACACAGACCACACAGACCACAGACAGACAGACTATAAGTGAATAGACTGTGCTTTAGCGACACGCTCT
     fMetLysLeuProArgSerSerLeuValTrpCysValLeuIleValCysLeuThrLeuIleLeuPheThrTyrLeuThrArgLysSerLeuCysGluIle
     Hok protein
                                                                                                  Ter Ter
401  TTCGTTACAGAGACGGACACAGGAGGAGGTGGCGGCTTTCATGGCTTACGAATCCGGTAAGTAGCAACCTAGAGGGGCAGGCCCGGCCTTTCAGGACT
     AAGCAATGTCTCTGCCTGTGTCCTCCACCGCCCGAAAGTACCGAATGCTTAGGCCATTCATCGTTGGATCGTTGGAATAGTCAAGTCGGGCCGGAAAGTCCTGA
     ArgTyrArgAspGlyHisArgGluValAlaAlaPheMetAlaTyrGluSerGlyLysTer
                                                                                    IV
501  GATGCTGGTCTGACTACTGATGAAGCGCCTTTATAAAGGGGCTGCTGGTTCGCCGGTAGCCCTTCTCCTTGCTGATGTTGT
     CTACGACCAGACTGATGACTTCCGCGGAAATATTTCCCCGACGACCAAGCGGCCATCGGGAGCCCTTTCTCCTTGCTGATGTTGT
                                                 V
```

Fig. 3b hok gene product
Met Lys Leu Pro Arg Ser Ser Leu Val Trp Cys Val Leu Ile Val Cys Leu Thr Leu Leu
Met Lys Gln Lys Ala Met Leu Ile Ala Leu Ile Val Ile       Cys Leu Thr Val Ile
relB-orf3 gene product Ile Phe Thr Tyr Leu Thr Arg Lys Ser Leu Cys Glu Ile Arg Tyr Arg Asp Gly His Arg
Val Thr Ala Leu Val Thr Arg Lys Asp Leu Cys Glu Val Arg Ile Arg Thr Asp Gln Thr Glu Val Ala Ala Phe Met Ala Tyr Glu Ser Gly Lys-COOH
Glu Val Ala Val Phe Thr Ala Tyr Glu Pro Glu Glu-COOH

Fig. 7a

```
251                                          .                              320
    TAGTCCACATCAGGATAGCCCTCTTACCGGCTTTGCGCGGCTTTGCGGCAAGGAGAAGAAGGCCATGAAACTACCACGAAG
    :  :   : ::    :   ::       :::     :::::::  ::::  :    :::::       ::    ::
    TGTTTCGCACCGAAGGTGACACTTCTGCTTGCGTTGACAGGAGAAGCAGGCTATGAAGCAGCAGCAAAA
    (1037)                                                 SD       Met
                                                                    Met

321                                          .                              390
    TTCCCTTGTCTGGTGTGTGTTGATCGTGTGTCTCACACTGTTGATATATTCACTTATCTGACACGAAAATCG
     :   ::  :  : :::    :   ::  :::  :   ::: :::  :   :  ::: ::: :  :::
    GATGTTAATCGCCCTGATCGTCATC    TGTTTAACCGTCATAGTGACGGCACTGGTAACGAGGAAGAC

391                                          .                              460
    CTGTGCGAGATTCGTTACAGAGACGGAGACACAGGGAGGTGGCGGCTTTCATGGCTTACGAATCCGGTAAGT
    :: ::::: :  :: :  :::  :: ::  :: :::::::::  :::    ::::  :::::::::  :::
    CTCTGCGAGGTACGAATCCGAACCGAGTCGCTGTCTTCACAGTCGCTTACGAACCTGAGGAGT

461                                          .                              530
    AGCAACCTAGAGGCGGGCCGCAGGCCCGCCCTTTTCAGGACTGATGCTGGTCTGACTACTGAAGCGCCTTTA
     :   ::  :::  ::::  :::    :::      :: :::  ::  :: :  :: ::  ::    ::::
    AAGAGACCCGGGCGGGGGAGAAATCCCTCGCCACCTCTGATGTGGCAGGCATCCTCAACGCACCCGCACTT
    Ter

531                                          .                              580
    TAAAGGGGCTGCTGGTTCGCGCGGTAGCCCCTTTCTCCTTGCTGATGTTGT
    :    ::  :::  :    :: :  :::::    :    ::  ::
    AACCCGCTTCGGCGGGTTTTGTTTTTATTTCAACGCGTTGAAGTTCT   (1363)
```

Fig. 7b

STABILIZATION OF UNSTABLY INHERITED REPLICONS

This application is a continuation of application Ser. No. 07/029,760, filed Feb. 13, 1987, now abandoned, which is a continuation of PCT/DK86/00070, filed Jun. 18, 1986.

TECHNICAL INTRODUCTION

Genetic stability, at the level of cell populations as well as at the level of the individual cell, is a universal feature in cell biology.

A major set of largely unknown control mechanisms governs the equal distribution of the cellular chromosomes to daughter cells upon cell division since unequal distribution of the chromosomes would lead to cell death or at least, in the case of eukaryotic cells, to an increased possibility of severe cellular disturbances.

However, not only the distribution of cellular chromosomes seems tightly controlled since extrachromosomal genetic elements (in essence to be considered to be minichromosomes) of prokaryotic as well as eukaryotic cells can be stably maintained in cell populations. The evolution of plasmids through the exchange of genetic information with host cell genomes may indicate a chromosomal origin of the genetic information governing the equal distribution of freely replicating molecules, especially those molecular species present in very few copies per cell or per compartment (organelle). Such putative chromosomal ancestors may not serve a similar purpose with regard to the problem of chromosome distribution although this is a tantalizing possibility.

Noticeably, the naturally occurring bacterial plasmids (e.g. R1), present in 1-2 copies per bacterial genome, face a distribution problem of the same magnitude as the bacterial chromosome. By implication, stringent control mechanisms must exist to ensure the stable maintenance of such plasmids in the population even in the absence of an exogenous selection pressure favouring the survival of those cells carrying the plasmid.

Plasmid replication control mechanisms regulate the plasmid concentration in growing cells, but without an ordered distribution of the plasmid molecules among daughter cells at cell division, the possibility that cell division would lead to a plasmid-free cell would be very significant, especially for plasmids present in only 1-2 copies per bacterial genome. Maintenance functions governing the ordered distribution of replicons have been termed partitioning functions.

An alternative replicon stabilizing function encoded by the ccd locus of plasmid F (Ogura and Hiraga, *Proc. Natl. Acad. Sci.*, 80, 1983, 4784–4788) was shown to involve inhibition of cell division in a situation where only one copy of the F plasmid was present at the time of cell division.

In eukaryotic cells, similar stability functions affecting freely replicating molecules may be encountered in three different situations. Firstly, the genomes of several naturally occurring viruses capable of infecting eukaryotic cells have the potential to exist in a plasmid state, although the natural course of the vital infection may prevent this occurrence. Plasmid genomes can be found in cells infected with e.g. Epstein-Barr virus, SV40 and polyoma viruses, the papilloma viruses, and certain retroviruses, especially the (HTLVIII) associated with the acquired immune deficiency syndrome and the Visna virus of sheep origin. Several of these viruses are used as gene vectors in eukaryotic cells.

Secondly, specific regions from eukaryotic chromosomes, e.g. of human origin, can be found as naturally occurring, extrachromosomally replicating minichromosomes ('double minutes') that are stably maintained during growth, the copy number ranging from a very few to several hundreds. Using a yeast plasmid unable to replicate in *Saccharomyces cerevisiae*, autonomously replicating sequences (ars) were identified by insertion into the plasmid of fragments of chromosomal DNA from various sources, e.g. yeast, Drosophila and *Zea mays* (Stinchcomb, D. T. et al., *Proc. Natl. Acad. Sci.*, 77, 1980, pp. 4559–4563) and such autonomously replicating sequences may be used to create novel replicons for a wide variety of cells, the crucial point being, however, the extent to which such replicons will be stably maintained in the cell population without exogenous selection pressures.

Thirdly, two types of organelles, the mitochondria and the plant chloroplasts, are basically self-renewing organelles containing their own, strictly compartmentalized genome; upon organelle division each newly formed organelle needs to be equipped with at least one copy of the organelle genome in order to function. Most mitochondrial species contain from 5 to 20 genomes, hence representing a genome distribution problem similar to that of bacterial plasmids with low or intermediate copy numbers, and the appearance of genome-free organelles might be expected to occur at a high frequency resulting in the appearance of non-functional organelles if the distribution is not tightly controlled. This expected loss of mitochondria by unequal genome distribution may be compensated for by the fact that most cell types contain a large number of mitochondria. A mechanism that secures the stable maintenance in the population of mitochondria of genetic information introduced into mitochondria by a gene vector may prove useful in attempts to genetically manipulate certain plant cells (Levings III, C. S. and Pring, D. R., in *Genetic Engineering*, 1, Ed. J. K. Setlow and A. Hollaender, Plenum Press, 1979, pp. 205–222). In plant chloroplasts, the number of chloroplast genomes varies from 20 to 80, i.e. a situation resembling that of the high copy number plasmids in bacteria, and furthermore, in most plant cells the number of chloroplasts is high. However, in Chlamydomonas only two chloroplasts are present per cell and despite the presence of 80 copies of chloroplast genome in each, a high degree of stability is required to secure the stable maintenance of the chloroplast genome. Genetic manipulations in higher plants may be possible using plant chloroplasts (Bogorad, L., in *Genetic Engineering*, 1, Ed. J. K. Setlow and A. Hollaender, Plenum Press, 1979, pp. 181–204).

The increasing interest in vectors designed to allow expression of foreign genes in eukaryotic cells makes the control mechanisms involved in genome maintenance in eukaryotic cell populations an important target of research.

The strategy developed by the present inventors has been to extract extensive knowledge about the concepts involved in plasmid stabilization from a well-defined system in *E. coli*, the R1 plasmid and to attempt extrapolation to 1) other replicons, 2) other unrelated bacteria, and 3) eukaryotic systems.

The current interest in replicon partitioning functions has arisen from instability problems frequently encountered when recombinant DNA techniques are applied on an industrial scale.

In prokaryotic systems, the design of cloning vectors from naturally occurring plasmids has primarily focused on obtaining a high copy number which, to a certain extent, also serves to maintain the plasmid stably in a population since the possibility of a plasmid-free cell appearing due to random distribution of plasmid molecules is reduced. It is well-documented, in prokaryotic as well as eukaryotic systems, that the insertion of foreign DNA into many otherwise stable cloning vectors may convert these into highly unstable recombinant plasmids. This may be due to a decrease in copy number or to growth-inhibitory effects of product(s) encoded by the inserted DNA. Since the feasibility of applying external selection pressures, i.e. to positively select plasmid-bearing cells, during industrial scale growth is rather limited, it seems essential to be able to manipulate the stability phenotype of the vector.

A step forward towards an improved understanding of the stable maintenance of plasmids in host cells was the finding that the parB region of the plasmid R1 is capable of converting unstable recombinant plasmids unrelated to R1 into stably inherited plasmids that are maintained in the *E. coli* population for hundreds of generations without any external selection pressure (cf. International Patent Application PCT/DK83/00086, Publication No. WO84/01172). The stabilization of plasmids by means of the parB region indicated an applicability of the resulting vectors in large scale production employing genetically manipulated bacteria since no external selection pressure is required to secure the maintenance of the plasmid during large scale growth.

DISCLOSURE OF THE INVENTION

The present invention relates, inter alia, to replicons which carry genetic information responsible for the stable maintenance of the replicon in a cell population, which information is either native to a given replicon or carried on an inserted fragment or fragments of nucleic acid; the replicons may further carry one or more inserted genes not naturally related to the replicons.

The parB stabilization is a very effective replicon stabilization mechanism which has the advantage that the whole mechanism is expressed from a sequence which is present on one and the same replicon. The present inventors have therefore searched for parB-like, stabilizing functions among plasmids with the same stability problems as R1 and for putative ancestors of the R1 plasmid stability systems in the chromosomal DNA of *E. coli* and of other prokaryotic as well as eukaryotic organisms, the ultimate goal being to select or construct, from such genetic information, stability control systems which are operative in a given organism. As shown by the initial results of this research discussed below, stabilization by parB has been found to be indicative of a general and very effective replicon stabilization mechanism which may be possible to establish in a wide variety of living cells.

The present invention is based on these findings and relates, in one aspect, to a replicon which, when harboured in a cell, expresses a product capable of killing the cell or its progeny (or a precursor for the product) and which further expresses an antagonist for the killing product (or a precursor for the antagonist), the antagonist being one which suppresses the killing product (or a precursor for the killing product) in cells harbouring the replicon, whereas the antagonist activity decays when the replicon is lost from the cells so that the antagonist (or its precursor) is no longer continuously expressed, which means that the killing product (or its precursor) present in the now replicon-free cell is no longer suppressed by the antagonist, resulting in cell death, with the proviso that the cell killing product as well as the antagonist therefor are not encoded by the R1 parB region when the replicon is a plasmid capable of replicating in gramnegative bacteria.

The parB region itself has previously been disclosed in, e.g., International Patent Application No. PCT/DK83/00086, Publication No. WO84/01172, in connection with demonstrating the stable maintenance of a variety of plasmids which replicate in gramnegative bacteria. As indicated in this patent application, the stabilizing effect was thought to be ascribable to a partitioning function expressed from the parB region. This partitioning function supposedly operated by a mechanism ensuring the ordered distribution of the plasmid molecules to the daughter cells at cell division. Recent research has demonstrated that the parB region is extremely effective in stabilizing many different types of unstably inherited plasmids which are then very rarely lost from the population in the absence of selection pressure. The stabilizing effect was further shown to be independent of plasmid replication, of the reasons for the instability and, to a large extent, of the bacterial host.

However, further research into the structure and molecular mechanism of parB has most surprisingly established a novel stabilization principle, which, as outlined above, comprises a cell killing function and an antagonist therefor. On the basis of hybridization experiments as described below, the novel stabilization principle is assumed to be active in most, if not all types of cells, and has the advantage of being highly versatile, which means that it may be applied to stabilize many different types of replicons which may be unstably maintained for many different reasons.

In the present context, the term "replicon" designates a segment of nucleic acid (DNA or RNA) which is able to replicate autonomously in a given host cell or in a given range of host cells. Thus, the replicon may for instance be a bacterial plasmid, a bacterial virus, a bacterial chromosome, a eukaryotic plasmid (RNA or DNA), a eukaryotic virus, a eukaryotic autonomously replicating sequence carrying a chromosomal origin of replication, a eukaryotic mitochondrial DNA molecule, or a eukaryotic chloroplast DNA molecule.

For most practical purposes in the technical exploitation of the invention, the replicon will not be a native replicon, but will be a replicon which contains one or more inserted nucleotide sequences which are not naturally related to the replicon and which have been inserted into the replicon by any recombinant DNA technique required for the replicon in question and the type of nucleotide sequence to be inserted. (The term "inserted" about a gene or fragment of nucleic acid indicates that the gene or fragment of nucleic acid has been introduced into the replicon at one stage during the construction of the final replicon). The inserted nucleotide sequence or sequences may for instance be a DNA sequence containing a gene expressing a product which it is desired to produce by means of a culture of cells, e.g. bacteria, containing the replicon, e.g. a plasmid. Such products comprise a wide variety of products for medical or technical purposes, particularly polypeptides and proteins or fragments thereof, enzymes and non-proteinaceous products of reactions of enzymes with a compound in the nutrient medium, hormones and other low molecular products. Products of eukaryotic, especially mammalian genes are of particular interest. The replicon may, however, also be a not previously isolated replicon in its native state, provided the replicon is useful either as a vector (into which a non-native gene may be inserted with a view to harvesting the gene product in question from a culture of cells harbouring the replicon containing the inserted gene) or as a production replicon if the replicon itself expresses a valuable product.

A search for regions analogous to parB in other systems has surprisingly established sequences homologous to parB in many different plasmids, bacterial genomes and even in eukaryotic cells, and the molecular mechanism behind the stabilizing effect as disclosed below form a solid basis for the assumption that a central cellular target, possibly conserved in all cells, interacts with a gene product from these homologous sequences (possibly conserved in all cells) in accordance with the same or a similar principle so that the parB homologous sequences may be used directly or after relatively simple genetic manipulations resulting in the construction of parB-like stabilizing regions to stabilize any given type of replicon in many different organisms. In the working examples, the evidence for this reasoning is presented.

In the present context, the term "precursor" indicates a product which, under the conditions prevailing in the cell at the appropriate time, either directly or indirectly gives rise to the product whose presence results in the function in question (either the killing function or the antagonist function).

The toxic substance may be a protein or a precursor therefor such as a pre-protein which has to be modified either by proteolytic cleavage or by the addition of a functional group (including a fatty acid residue) in order to become toxic, or an mRNA whose translation results in a toxic protein.

The antagonist may be a gene product, either RNA or protein, which suppresses the activity of the toxic substance by combining with it directly or interfering with its target in the cell, or it may be one which suppresses the conversion of the precursor for the toxic product, i.e. pre-protein, or the translation of the mRNA into the actual toxic product.

In most or all living cells there are genes whose products, when substantially overexpressed, will be lethal or growth inhibiting to the cell, and which therefore may be used for replicon stabilization in the manner described above.

The mechanism which has now been found to be exerted by the R1 parB region is a killing/antagonist mechanism of the above-identified type. Thus, the mechanism is based on products expressed from two genes present within the R1 parB region, one gene (the R1 parB hok gene as described below) expressing a product capable of killing the cell, and a second gene (the R1 parB sok gene, as described below) expressing a product that antagonizes the hok gene product in cells harbouring a replicon from which the R1 parB genes are expressed, whereas, in the absence of continued expression of the antagonist, for instance caused by loss of the replicon, the antagonist activity decays so that the killing product (which has a longer half-life in the cell than the antagonist) is no longer suppressed by the antagonist (i.e. the translation of the mRNA coding for the killing product is no longer inhibited). Evidently, this type of mechanism results in the death of cells which have lost the replicon from which the antagonist function is expressed so as to ensure that the population of cells will not contain proliferating cells not harbouring the replicon, which in turn implies that the living and proliferating cells of the population will be cells harbouring the replicon; in this way the stable maintenance of the replicon in the population is ensured.

As a result of further research into the parB mediated stabilization, it was surprisingly found that the mechanism governing the stable maintenance of a replicon in a cell population implies the regulated expression of a host cell killing function. Stabilization mechanisms involving the regulated expression of a host cell killing function have been described before, but in all known cases they have involved a separation of the gene encoding the antagonist (e.g. on a plasmid) from the gene encoding the toxic product (e.g. on the chromosome), and the killing function has been restricted to one or a very few organisms (see for instance European Patent Application No. 82306207.0, Publication No. 0 080 848).

According to the present invention, the above-identified principle underlying, e.g., the R1 parB plasmid stabilization function, is applicable in a wide range of replicons and hence in a wide range of host cells, prokaryotic as well as eukaryotic, as a means of obtaining stable maintenance of the replicon in question in a given cell population.

Two aspects of the parB system are highly important for 1) the general applicability of this type of stabilization system in living cells and 2) the possibility of constructing stabilization systems corresponding to the parB system which may function in a very broad spectrum of organisms:

1. The unexpected finding of homologous sequences in most/all bacteria as well as in various eukaryotic organisms, which agrees with the assumption that the target for the lethal function of the hok product is fundamental to most, if not all living cells.

2. The unique nature of the regulatory mechanism which ensures the survival of all plasmid carrying cells, and the rapid killing of any plasmid-free cell that appears. Based on genetic evidence, it is believed that the actual sok-encoded regulator substance is an RNA molecule which inhibits translation of hok-encoded mRNA. If one assumes that the sok-encoded RNA is more unstable than hok-encoded mRNA, the inhibition of translation of the hok-encoded mRNA will gradually decrease in a cell which has lost the $parB^+$ plasmid and the hok-encoded protein will eventually kill the cell.

On the basis of these assumptions, it is contemplated that i) the parB region, or any very similar region derived from replicons other than R1, which includes both the hok and sok genes, or analogues of these, should stabilize the maintenance in all types of bacteria of all types of plasmids into which it is inserted. This has been confirmed since many different plasmids have been stabilized by a factor of more than 100 in *E. coli* after the insertion of parB, and in a bacterium phylogenetically very distant to *E. coli*, such as *Pseudomonas putida*, the parB region was found to be as effective as in *E. coli*.

ii) Plasmids other than R1, from bacteria other than *E. coli*, may carry sequences which are substantially homologous to parB. It is likely that such sequences may be used in a similar fashion for plasmid stabilization purposes. The rationale behind this is that the hok gene is homologous to a chromosomal relB-orf3 gene, which expresses a product whose activity is identical to that of the hok gene which supports the theory that the gene has transposed from the chromosome to the plasmid where it eventually evolved into the parB system. This makes it reasonable to assume that the same process may also have taken place in other replicons. The hybridization experiments strongly indicate that this is in fact the case, since several plasmids unrelated to R1 as well as chromosomal DNA from bacteria other than *E. coli* carry parB homologous sequences.

It should be noted that a chromosomal sequence from *E. coli* which is 55% homologous to parB within the hok coding region, yet undetectable by hybridization with the parB probe used, yields a Hok phenotype, which confirms the above statements.

iii) It would be possible to construct a parB-like system by first isolating the hok gene analogue from either a plasmid or chromosome followed by superimposing a regulatory loop similar to the one represented by sok in parB; the construction may be carried out by inserting a short synthetic DNA sequence (including a promoter) which, when transcribed, expresses a small antisense-RNA complementary to the part of the hok-mRNA or hok-analogue mRNA which harbours the ribosome binding site. Pairing of the antisense-RNA to the mRNA inhibits translation of the mRNA and hence cell death. Several such natural regulation systems (where an antisense RNA inhibits the translation of an mRNA) have previously been described e.g. Light and Molin, *The EMBO Journal* 2, No. 1, 1983, pp. 93–98, and artificial systems like the one proposed above have also been successfully implemented. Thus, the proposed strategy is logical and realistic and may be applied to, for instance all known bacteria.

In accordance with the explanation given above, the replicons of the present invention may be replicons pertaining to many different types of cells, such as a bacterial plasmid, a bacterial virus, a bacterial chromosome, a eukaryotic plasmid (RNA or DNA), a eukaryotic virus, a eukaryotic autonomously replicating sequence carrying a chromosomal origin of replication, a eukaryotic mitochondrial DNA molecule, or a eukaryotic chloroplast DNA molecule. Correspondingly, the sequence in the replicon which specifies the killing product may suitably be a sequence from a corresponding system, such as from a bacterial plasmid, a bacterial chromosome, a eukaryotic plasmid, a eukaryotic virus, a eukaryotic autonomously replicating sequence carrying a chromosomal origin of replication, a eukaryotic mitochondrial DNA molecule, or a eukaryotic chloroplast DNA molecule.

Similarly, the sequence encoding the antagonist for the killing product may be derived from a bacterial plasmid, a bacterial chromosome, a eukaryotic plasmid, a eukaryotic virus, a eukaryotic autonomously replicating sequence carrying a chromosomal origin of replication, a eukaryotic mitochondrial DNA molecule, or a eukaryotic chloroplast molecule, or may be a synthetic sequence.

Interesting replicons according to the invention are replicons carrying sequences which operate analogously to the R1 parB system so that, when harboured in a cell, they express a messenger RNA encoding a product which is capable of killing the cell or its progeny and further express an antagonist inhibiting the translation of the messenger RNA in cells harbouring the replicon. When the replicon is lost from the cell, the antagonist (or its precursor) is no longer continuously expressed and its activity decays so that the translation of the messenger RNA present in the now replicon-free cell is no longer inhibited by the antagonist. Among these, interesting replicons are replicons which express an antisense RNA molecule acting as the antagonist which through base pairing to at least part of the messenger RNA encoding the cell killing product prevents translation of the messenger RNA.

In accordance with what has been stated above, particularly interesting embodiments of the invention are replicons which are DNA molecules comprising a sequence which encodes a product (or a precursor for the product) capable of killing the cell or its progeny in a manner identical with or analogous to that of the product (or precursor) expressed by the R1 parB hok gene. Such replicons further comprise a sequence encoding an antagonist which functions in a manner identical with or analogous to that of the antagonist which is expressed by the R1 parB sok gene. Thus, in some replicons according to the invention, in particular bacterial plasmids, the R1 parB region may be used as such to secure the maintenance of the replicon, or it may be suitably modified to secure proper expression of its hok and sok genes in the host bacterium in question, for example by suitable changes in the promoters from which these genes are transcribed.

Alternatively, a fragment of nucleic acid expressing a mechanism securing replicon maintenance in a population in a manner identical to or analogous with the above-identified mechanism may partly or completely be obtained from DNA or RNA more closely related to the host cell in question. A recommended strategy would be to select, from the genome of a given host cell or from DNA or RNA of replicons harboured by the host cell, such nucleic acid sequences which are homologous to the R1 hok gene or to any gene homologous to R1 hok, which when expressed is capable of killing the host cell from which the gene has been isolated. Such sequences may be used in experiments designed to test for the presence of hok- and sok-like activities in the host cell in question. If both activities are found, this implies the existence of a useful replicon stabilizing region within the isolated sequences, whereas, if only a hok gene-like activity is found, it is possible to construct the necessary regulatory loop (i.e. the antagonist) according to the strategy outlined above, thereby converting a potential cell killing function into a potentially useful replicon stabilizing function.

The sequence which expresses the product capable of killing the cell or its progeny may be inserted separately from the sequence which expresses the antagonist, or the two sequences may be present on one nucleic acid fragment which is the case with, for instance, a DNA fragment comprising the R1 parB region. The nucleic acid fragment may be inserted into the replicon by any recombinant DNA technique which is suitable for the type of replicon in question and for the type of nucleic acid comprising the stabilizing function.

Thus, one aspect of the invention relates to a DNA fragment comprising a sequence which encodes a product capable of killing a cell or the progeny of a cell harbouring a replicon carrying said fragment (or encodes a precursor for the product) and a sequence encoding an antagonist for the killing product (or encoding a precursor for the antagonist), the antagonist being one which suppresses the killing product (or a precursor for the killing product) in cells harbouring the replicon, whereas the antagonist activity decays when the replicon is lost from the cell so that the antagonist (or its precursor) is no longer continuously expressed, which means that the killing product (or its precursor) present in the now replicon-free cell is no longer suppressed by the antagonist, resulting in cell death. An interesting embodiment of this aspect is constituted by a DNA fragment comprising a sequence which encodes a messenger RNA for a product capable of killing the cell or the progeny of the cell harbouring the replicon carrying said fragment (or encodes a precursor for the product) and a sequence encoding an antagonist inhibiting the translation of the messenger RNA in cells harbouring the replicon. When the replicon is lost from the cell, the antagonist (or its precursor) is no longer continuously expressed, and its activity decays so that the translation of the messenger RNA present in the now replicon-free cell is no longer suppressed by the antagonist.

The invention also relates to a living cell harbouring a replicon as identified above, and to a cell culture containing such a living cell. The cell may be a bacterium, a unicellular eukaryotic organism, an animal cell or a plant cell.

Although, in accordance with the invention, it is most advantageous to provide the killing function and the antagonist therefor on the same replicon as this ensures a more easy applicability of the stabilization principle of the invention, it is further contemplated that the sequences coding for the Hok and Sok gene products, respectively, or sequences homologous therewith may be inserted on separate replicons in such a way that the stabilizing function of the invention is expressed when the replicons are introduced in a host cell. In order to get proper expression, it may be necessary to suitably modify the promoter sequences of either or both genes. Thus, in another aspect, the present invention relates to a living cell harbouring one replicon which comprises the R1 parB hok gene or a sequence homologous therewith and another replicon which comprises the R1 parB sok gene or a sequence homologous therewith. It should be noted that, in the present context, the term "sequence homologous therewith" is understood to mean a sequence which is either homologous with one of the parB genes themselves or homologous with any sequence which is homologous with one of the parB genes.

In principle, the hok and sok genes or the homologous sequences may be present on any two different replicons provided that these may coexist compatibly in the same cell. However, the hok or hok homologous gene is preferably present on a replicon which in itself is stably maintained in the cell, such as a chromosome, while the sok or sok homologous gene is most advantageously inserted on the replicon the stable maintenance of which is desired, that is, typically the replicon expressing a desired gene product. The replicon carrying the sok or sok homologous gene is therefore usually an extrachromosomal, autonomously replicating nucleotide sequence, for instance a plasmid. Loss of the replicon carrying the sok or sok homologous gene from the cell so that the sok gene product is no longer continuously expressed causes cell death in accordance with the principles described above which means that only cells harboring this replicon are viable.

The invention also relates to a method for preparing a stabilized replicon as defined above, the method comprising inserting, into a replicon, a sequence which encodes a product capable of killing a cell harbouring the replicon or the progeny of the cell (or encoding a precursor for the killing product) and a sequence which encodes an antagonist for the killing product (or which encodes a precursor for the antagonist), the antagonist being one which suppresses the killing product (or a precursor for the product) in cells harbouring the replicon, whereas the antagonist activity decays when the replicon is lost from the cell so that the antagonist (or its precursor) is no longer continuously expressed which means that the killing product (or its precursor) present in the now replicon-free cell is no longer suppressed by the antagonist, resulting in cell death, with the proviso that the cell killing product as well as the antagonist therefor are not encoded by the R1 parB region when the replicon is a plasmid capable of replicating in gramnegative bacteria.

In accordance with the above explanation, the sequence or sequences inserted may be a sequence or sequences of DNA (or, where applicable, RNA) originating from a cell related to the replicon, in particular a sequence or sequences homologous with the R1 parB region, or the sequence or sequences may originate from the R1 parB region, possibly with modified promoter functions to adapt the sequence to the particular cell type in which the replicon is to be harboured.

The invention also relates to a method for preparing a gene product encoded by a nucleic acid sequence, the method comprising cultivating cells harbouring a replicon as defined above, and harvesting a gene product expressed from the replicon. The cultivation should be performed in a nutrient medium suitable for the cell type in question, that is, a medium containing the necessary nutrients for that cell type. The cultivation will normally be performed for a large number of generations, e.g. more than 100, in order to obtain a sufficient production of the valuable product encoded by the nucleic acid sequence, and during this cultivation, the loss of the replicon will decrease dramatically due to the replicon stabilization function defined herein compared to the loss encountered if no replicon stabilization mechanism had been utilized. Thus, it is realistic to have a loss of the stabilized replicon of less than $10^{-4}$ cell/generation, normally less than $10^{-5}$ cell/generation and often less than $10^{-6}$ cell/generation.

In all instances cited above, the invention is based on the ability of nucleotide sequences, such as parB or parB-like sequences, to mediate a phenotype of stable maintenance in a cell population of a replicon carrying the sequences. The stabilization-mediating sequences should be inserted in the replicon in such a way that the killing function and the antagonist function, encoded by for instance the hok or hok-like and sok or sok-like genes, are expressed. In order to be effective, it may be advantageous to select the sequences according to the type of host cell involved, e.g. bacteria, yeasts, fungi, animal cells or plant cells, and it may be necessary to modify or artificially re-create the proper regulatory loop, such as the sok or sok-like regulatory loop. The resulting stabilization mechanism will operate in accordance with the principles described above, especially in a way which is analogous with the mechanism explained for R1 parB. Since the crux of the replicon stabilization mechanism is that cells which have lost the replicon are killed by means of the killing product, e.g. the hok gene product, the present invention has the important industrial utility due to the independence of the described replicon stabilization mechanism of any external selection pressure, e.g. the addition of specific nutrients, antibiotics or other changes in the cellular environment, during large scale growth of cells comprising multiple generations of cell proliferation.

Another important advantage of the present invention is the independence of the described replicon stabilization mechanism of any specific combinations of host cell and replicon vector which is necessary in the system disclosed in European Patent Application No. 82306207.0, Publication No. 0 080 848. In the technical exploitation of the present invention, a broad spectrum of replicon/host cell systems may therefore be considered. The general strategy for creating a replicon-maintaining system, e.g. a system identical or analogous with the R1 parB system has been described above and will be exemplified in the following.

1. Gramnegative and grampositive bacteria

Suitable replicons in bacterial host cells may for instance be plasmids capable of replicating in Enterobacteriaceae, e.g. pBR322 or R1 runaway replication plasmids (European Patent Application No. 83305438.0, Publication No. 0 109 150), or capable of replicating in gramnegative bacteria in general, e.g. plasmids derived from RSF1010 (Bagdasarian et al., *Gene* 16, 1981, pp. 237–242), or plasmids capable of replicating in grampositive bacteria such as *B. subtilis*, e.g. pC194 and pUB110 (Lovett and Keggins, *Meth. in Enzymol.* 68, 1979, pp. 342–357), all of which may be unstably inherited when used as cloning vectors. In order to stabilize such bacterial plasmids by a parB-like mechanism, a DNA fragment or DNA fragments comprising the R1 parB region can be inserted into the replicon in such a way that the R1 hok and sok expression is transcribed from the native promoters of R1 parB. If the R1 hok and sok genes are not transcribed from these native promoters in the host cell in question, e.g. due to differences in promoter sequence requirements between *E. coli* and other bacteria, the native promoter sequences of R1 parB may be substituted by promoters known to be recognized in the host cell in question, such promoters being either natural promoters or synthetic promoters, such as the SPO2 phage promoter active in *B. subtilis* (Williams et al., *Gene* 16, 1981, pp. 199–206). If the R1 hok gene product is not lethal to the host cell in question—an absolute requirement in order to establish the replicon stabilization function of R1 parB—an R1 hok analogous sequence may be isolated from either the genome of the host cell in question (or a closely related bacterial species) or from a plasmid naturally occurring in the host cell in question (or a closely related bacterial species) and subsequently tested for cell killing activity in a manner similar to that described in the Examples for one *E. coli* chromosomal homologue of R1 parB, followed by the construction of a regulatory loop regulating the expression of the newly isolated parB homologue so as to create a replicon stabilization system specifically adapted to the host cell involved when the construct is inserted into the replicon in question.

The use of the hok/sok system or a system analogous to the hok/sok system in bacteria thus includes: a suitable selection of replicon and host cell; insertion into the replicon of the proper sequence comprising a hok/sok system or a system analogous to the hok/sok system which is expressed in the selected host cell; insertion into the stabilized replicon of a gene or genes encoding one or more useful products to be produced on a large scale; introduction of the stabilized recombinant replicon into the bacterial host cell by standard techniques of bacterial transformation; cultivation of the replicon-containing host cells in a culture medium supplemented with the necessary nutrients for the number of generations, e.g. more than 100, required to reach the desired cell density; and, finally, harvesting the cells and the medium from either of which the resulting product may be isolated. It should be emphasized that the mechanism of replicon stabilization to which the present invention relates does not require any manipulation of the culture during growth in order to secure the maintenance of the stabilized replicon in the population since cells from which the replicon is lost are killed by the hok or hok-like product expressed in the replicon-free cell.

2. Yeast cells

The technical exploitation of recombinant DNA techniques in eukaryotic systems may be desired to obtain such post-translational modifications (specific proteolytic cleavages, glycosylation, etc.) of primary (eukaryotic) gene products, which modifications are either not made in bacteria at all or, at best, are only made in a suboptimal way. A widely used eukaryotic organism is the yeast *Saccharomyces cerevisiae* in which a naturally occurring plasmid, the 2µ replicon, has been adapted as a vector for expression of genes not naturally related to the 2µ replicon in *Saccharomyces cerevisiae*. Recombinant DNA molecules comprising the 2µ replicon with one or more inserts of unrelated DNA fragments are often found to be unstably inherited in the yeast cells. According to the principles outlined above it is possible to isolate or construct a sequence to be inserted into a yeast replicon, e.g. the 2µ replicon, which sequence utilizes the principle of replicon stabilization by means of R1 parB, in order to stabilize the yeast plasmid.

Although the native promoters of the R1 hok and sok genes are not likely to be effective in *Saccharomyces cerevisiae* cells, the conservation of hok-like sequences over great distances of evolution indicated by the discovery of hok homologous sequences in a wide variety of organisms makes it realistic to test the product of R1 hok gene and of genes related to R1 hok (e.g. relB-orf3 or parl or other genes originating from bacterial genomes, and showing a homology at the sequence and functional level to R1 hok or similar genes isolated from bacterial plasmids) for its ability to kill yeast cells, such as *Saccharomyces cerevisiae*. In practice, this will entail isolating the coding region of the hok gene or hok-like gene and linking the coding region to a suitable yeast cell promoter such as the TRP1 promoter (Dobson et al., *Nucleic Acids Res.* 11, 1983, pp. 2287–2302), the resulting replicon being finally introduced into yeast cells according to standard methods, and the effect of the expression of the hok or hok-like gene is investigated. If cell death ensues, a useful hok or hok-like gene has been identified.

Alternatively, sequences identified in yeast DNA from yeast and homologous to parB or relB-orf3 may be isolated, linked to a proper yeast cell promoter, inserted into the 2µ replicon and, after the recombinant replicon has been introduced into *Saccharomyces cerevisiae*, tested for their ability to kill the cell. From a hok gene or a hok-like gene shown to be toxic to yeasts such as e.g. *Saccharomyces cerevisiae* when expressed, a replicon-stabilizing system identical or analogous with the R1 parB system may be generated by imposing a regulatory loop (e.g. a sok or sok-like gene regulated by an appropriate yeast promoter) as previously described in the discussion of the general strategy. The resulting yeast hok/sok sequence or hok/sok-like sequence may be inserted in any yeast replicon, e.g. the 2µ replicon or derivatives thereof into which genes not naturally related to 2µ have been inserted with the purpose of obtaining expression of the inserted genes, in order to secure the stable maintenance of the replicon or the derivatives hereof during growth. The thus stabilized replicon may be introduced into yeast cells, e.g. *Saccharomyces cerevisiae* cells, by transformation or protoplast fusion, and after selection, cells carrying the stabilized replicon may further be grown into a large scale culture in an appropriate culture medium supplemented with the necessary nutrients. No external selection pressure will be required to secure replicon stabilization, since cells from which the replicon is lost are killed by the hok or hok-like product expressed in the replicon-free cell. The culture consisting solely of cells harbouring the replicon is then harvested and any useful product expressed from the replicon may be isolated from either the yeast cells or the culture medium, depending on the nature of the gene and the gene product in question.

3. Mammalian cells

The requirement for specific post-translational modifications may necessitate the expression of certain eukaryotic genes in mammalian cells, i.e. of human or animal origin, rather than in bacteria or unicellular eukaryotic organisms. Replicons that may be used as cloning vectors in eukaryotic cells are derived from chromosomes (ars replicons), from DNA viruses, e.g. SV40 and bovine papilloma virus, or from RNA viruses, e.g. retroviruses. The two DNA viruses mentioned can be maintained in a plasmid state in infected cells while most retroviruses (RNA-containing viruses) need to be genetically modified in order to exist as freely replicating DNA molecules rather than chromosomally integrated copies of the viral RNA genome. It may be anticipated that the same problems of stable maintenance of the replicon involved as discussed above will occur during large scale growth of cells containing the above mentioned replicons into which genes not naturally related to the replicon have been inserted in order to obtain expression of a useful product.

A sequence containing a hok/sok system or a system analogous with hok/sok may be constructed similarly to that described for the yeast cell system, once a gene exerting a hok or a hok-like effect in the selected host cell has been identified. A first step would thus be to insert the coding sequence of known hok or hok-like genes, irrespective of their origin, from bacterial genomes or yeast cell genomes into a replicon capable of replicating in the host cell in such a way that expression of the hok gene is obtained on induction of expression. This means that the sequence coding for the hok or hok-like product should be supplemented with all necessary regulatory sequences required for expression of a gene in the host cell. A promoter sequence suitable for insertion upstream of the hok or hok-like gene may be the mouse mammary tumor virus LTR (long terminal repeat sequence) which is inducible with steroid hormones. If cell death ensues when transcription is induced, a hok gene or a hok-like gene has been identified for the host cell in question, and from this hok or hok-like gene, a replicon stabilization system may be constructed by imposing a regulatory loop, e.g. the sok or sok-like loop, as described above.

If none of the available hok or hok-like genes of bacterial or yeast origin exert a toxic effect in the mammalian host cells in question, novel hok-like sequences may be isolated from a mammalian genome (e.g. the sequences discovered in Tetrahymena mitochondrial DNA and in human cellular DNA) and subsequently tested for hok-like activity when properly expressed. The recommended strategy for the detection of novel hok-like sequences has been outlined above.

The use of the hok/sok-like stabilization mechanism in mammalian cells thus involves: selection of a suitable replicon, e.g. a retroviral vector able to exist as a freely replicating molecule as has been described for certain retroviruses, and selection of host cells dependent on the actual sequences regulating the expression of the inserted hok/sok-like genes; insertion into the stabilized replicon of such foreign genes which code for one or more desired products to be produced into the replicon; introduction of the stabilized recombinant replicon into the selected mammalian cell line by standard techniques of DNA transfection or microinjection; selection of cells containing the replicon; growth of the cells in a culture medium adapted to the cell line involved by the addition of necessary nutrients and growth factors with a view to obtaining a large scale culture of cells expressing the gene encoding the useful product; and, finally, harvesting the culture and isolating the desired product.

It should be noted that for any given fragment shown to express a stabilizing function when inserted in a replicon, it is possible to test whether the resulting stable maintenance of the replicon is ascribable to a stabilization mechanism according to the present invention in the following way:

inserting the fragment expressing the stabilizing function to be tested into a conditionally replicating vector, such as a rep(ts) vector, capable of replicating in a given type of host cell, growing the cells harbouring the vector under conditions where the vector no longer replicates, but where cell growth still takes place so that the vector is eventually diluted out of the cells, and determining the number of viable cells compared to a control harbouring the same vector which, however, does not carry the fragment. If the viability count is significantly lower than that of the control, as a result of the gradual decay of the antagonist in the vector-free cells, a stabilization mechanism according to the invention has been identified. An example of this test procedure is decribed in Gerdes et al., "Unique type of plasmid maintenance function: Postsegregational killing of plasmid-free cells", *Proc. Natl. Acad. Sci. USA* 83, 1986, pp. 3116–3120.

In connection with carrying out this test, it may also be possible to carry out a hybridization test for a possible homology of the fragment to R1 parB or a parB homologue.

While particular types of replicons adapted to particular types of cells have been discussed in detail above, the general principle of utilizing the stabilizing mechanism of the invention is the same, irrespective of the type of replicon and cell harbouring the replicon: the establishment, on the same replicon, of a host killing function and an antagonist function balanced so as to suppress the host killing function in cells harbouring the replicon, thus securing the stabilization of the replicon in the cell population.

DESCRIPTION OF THE DRAWINGS

The invention is further described with reference to the drawings, where

FIGS. 3*a* and 3*b* show the nucleotide sequence of the parB region. The 3' end of the upper DNA strand is positioned at right. The numbering of the bases is in accordance with the coordinates of the parB region in FIG. 1. Ter denotes the stop codon of the open reading frame present in the nucleotide sequence consisting of more than 50 codons. fMet corresponds to the start codon of the open reading frame. The amino acid sequence of the hok gene product, starting at position +304, is shown below the DNA sequence—the amino acid abbreviations are standard nomenclature. The sequences designated "–10" and "–35" are the promoter structures of the hok and sok genes. phok and psok denote the hok and sok promoter, respectively. Roman numerals denote stem-loop structures with the horisontal arrows on either side denoting the sequence of the stem-loop structures. Vertical arrows denote the termination of hok mRNA. The horizontal arrow positioned at 130 in FIG. 3A indicates the start of the hok transcript and the arrow at 258 indicates the start of the sok transcript.

FIG. 7a is a comparison of the amino acid sequences of the hok gene product and the relB-orf3 gene product, designated by Hok and RelB-orf3, respectively. Conserved amino acids are with bold face types; amino acids representing conservative changes are underlined.

FIG. 7b shows the alignment of the nucleotide sequences of parB and orf3 of the E. coli relB-orf3 operon (Bech et al. The EMBO Journal 4, 1985, pp. 1059–1066). The parB sequence is the upper strand, relB-orf3 the lower, coordinates of the parB as in FIG. 3. Vertical bars indicate conserved nucleotides. Numbers in brackets are the coordinates of the relB-orf3 nucleotide sequence as given by Bech et al supra. The two sequences are aligned so that the start codons of the two reading frames are at the same position— this is indicated with Met at position +304. The termination codons of the two reading frames are indicated with Ter at position 460–462.

MATERIALS AND METHODS

Figure 1:
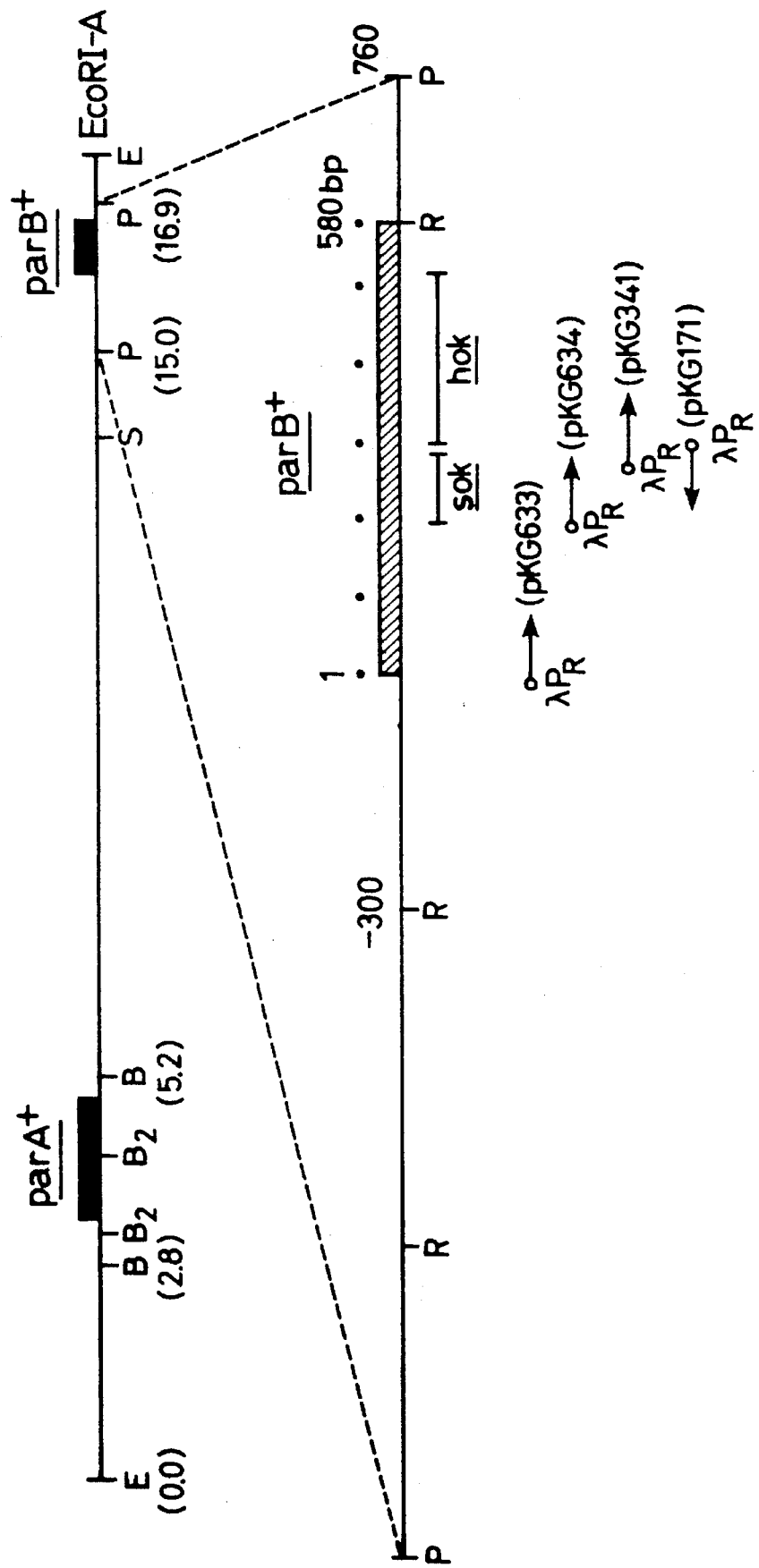
FIG. 1 shows a deletion map of the parB region. The localization of the parA region and the parB region within the EcoRI-A fragment of plasmid R1 are shown as black bars. Restriction enzyme sites in the EcoRI-A fragment are as described in now U.S. Pat. No. 4,806,471 cited in International Patent Application No. PCT/DK83/00086, Publication No. WO 84/01172 now U.S. Pat. No. 4,760,022. The parB region is located within the 1.9 kb PstI fragment bounded by coordinates 15.0 to 16.9. The parB region was further mapped to the right-hand 580 bp of an 880 bp RsaI fragment. The hatched region indicates the minimal parB region. The position of the hok and sok genes within the 580 bp parB region is also shown. A BglII-SalI fragment containing the λpR promoter and the cI857 allele of the λ repressor gene was inserted into pBR322 derivatives carrying various parts of the parB fragment. The position of the inserted fragments and the direction of transcription from λpR are shown below the map of the parB region (arrows). The λpR promoters in pKG633, pKG634 and pKG341 read from left to right into the parB region whereas the λpR promoter in pKG171 reads from right to left. Restriction enzyme sites are shown as E (EcoRI), B (BalI), $B_2$ (BglII), S (SalI), R (RsaI), and P (PstI).

Bacterial strains and plasmids.

The following *E. coli* K-12 strains were used: CSH50 ((lac-pro) rpsL), JC411 (metB leu his argG lacY malA xyl mtl gal rpsL), LE392 (Murray et al., *Mol. Gen. Genet.* 150, 1977, p. 53) and HB101 (F. Bolivar and K. Bachman, *Methods Enzymol.* 68, 1979, p. 245). JC411 was mainly used in the physiological experiments. CSH50 was mainly used for the genetic experiments. Furthermore, *B. subtilis* strain BD 224 (trpC2, thr-5, rec-4) (Dubnan & Cirigliano, *J. Bact.* 117, 1974, p. 488) was used for experiments with grampositive bacteria. The plasmids used are listed in Table 1. Bacteriophage λL47 (W. A. M. Loenen & W. J. Braunner, *Gene* 8, 1979, pp. 69–80) was used for plaque hybridization.

The experimental techniques used were standard techniques employed in the fields of microbial genetics (J. Miller: *Experiments in Molecular Genetics*, Cold Spring Harbor, New York, 1972) and genetic manipulation (Davis, Botstein and Roth: *A Manual for Genetic Engineering; Advanced Bacterial Genetics*, Cold Spring Harbor, New York, 1980, and Maniatis, Fritsch and Sambrook: *Molecular Cloning*, Cold Spring Harbour, New York, 1982).

All cells were grown in LB medium (Bertani, *J. Bact* 62, 1951, p. 293) with 0.2% of glucose and 1 µg/ml of thiamin, or A+B minimal medium (Clark and Maaløe, *J. Mol. Biol.* 23, 1967, p. 99) supplemented with 0.2% of glucose and 1% casamino acids. The plates used were LA plates containing LB medium and 15% of agar.

McConkey lactose indicator plates were prepared as recommended by the manufacturer (Difco), and X-gal plates were prepared by adding 20–40 µg/ml of 5-bromo-4-chloro-indolyl-β-D-galactoside to A+B minimal medium supplemented with 0.2% of glucose and 1 µg/ml of thiamin.

Physico-chemical methods

Clear lysates were prepared according to the method described by Clewell and Helinski, *Proc. Natl. Acad. Sci. USA* 62, 1969, pp. 1159–66.

Small scale preparation of plasmid DNA was performed by the method of Birnboim et al., *Nucl. Acids Res.* 7, 1979, pp. 1513–23.

Large scale preparation and analysis of plasmid DNA was performed by means of dye boyant density gradient centrifugation according to Stougaard and Molin, *Anal. Biochem.* 118, 1981, p. 181.

The restriction endonucleases were used in accordance with the prescriptions provided by the manufacturer (Boehringer, Mannheim or New England Biolabs Inc.) at 37° C. Double and triple digests were performed by starting with the enzyme requiring the lowest salt concentration and then adjusting with additional buffer before adding the next enzyme.

Treatment with the exonuclease Bal31 was performed as follows: 0.1 unit of Bal31 was added to 50 µg linear DNA and samples were taken out at 1, 2, 4, 8, 16, 32 and 60 minutes to 60 mM EDTA, extracted with phenol, ethanol precipitated and resuspended in 20 µl TE buffer. Half of the 20 µl was digested with the appropriate restriction enzyme subjected to agarose gel electrophoresis to determine the average size of the deleted DNA deletions. To the other half, the appropriate linker was added and the mixture ligated for 48 hours with an excess of T4 DNA ligase.

Ligation of restricted plasmid DNA was performed as recommended by the manufacturer with the exception of blunt end ligation, where an excess of T4 DNA ligase and ATP was added.

Measurements of β-galactosidase activity expressed from fusion plasmids were made from exponentially growing cultures, essentially as described by Miller, op.cit. Activity units were expressed as OD420 per minute per ml culture. Rifampicin (Ciba-Geigy) was added in high concentrations (300 µg/ml) to the non-permeable strain CSH50. Induction of the lac operon by adding IPTG (1 mM) to an exponentially growing culture of CSH50 (F'lac) and simultaneously adding rifampicin (300 µg/ml) showed that LacZ synthesis stopped within the first minute after the antibiotic had been added.

For the preparation of RNA, culture samples (10 ml) were removed and rapidly cooled to 0° C., spun in a Sorvall SS34 rotor and resuspended in TE buffer containing 0.2% SDS, phenol extracted twice, chloroform extracted three times, ethanol precipitated and resuspended in 200 µl TE buffer.

Mapping of RNA termini using S1 nuclease was accomplished essentially as described by Maniatis et al., op.cit. DNA-RNA hybrids were treated with an excess of S1 enzyme (100 units) at 20° C. overnight. End-labelling of DNA was accomplished by standard methos (Maniatis et al. op.cit.)

The calculation of mRNA half-lives from the rifampicin induction curves was carried out according to M. L. Pato, P. Bennett, K. von Meyenburg, *J. Bact.* 116, 1973, pp. 710–718. The residual capacity of protein synthesis (expressed in β-galactosidase units), which is directly proportional to the concentration of the mRNA (i.e. the hok'-lacZ hybrid mRNA) in the cell, was determined as the distance from the induction curve to the end plateau (reached at infinite time). These protein synthesis capacity values were plotted on a semilogarithmic scale versus time. This type of plot always yielded straight lines, from which the half-life of the mRNA could be read.

Construction of inducible parB derivatives (see also Table 1)

pKG633: The SalI-BglII fragment of pOU82 containing the cI857 temperature sensitive allele of the λ repressor gene and the λpR promoter was inserted into pPR633 in front of the parB region so that the λpR promoter reads into the region from left to right (FIG. 1). In an analogous way, the SalI-BglII fragment of pOU82 was inserted into pPR634 and pPR341, which are Bal31 deletion derivatives of pPR633, resulting in pKG634 and pKG341. pKG171: In pPR171, the SalI-BglII fragment of pOU82 was inserted in the opposite orientation, resulting in pKG171. The positions and orientations of the inserted λpR promoters relative to the hok and sok genes are shown in FIG. 1. pF634: The EcoRI-SalI fragment of pKG634 containing the right 390 bp of the parB region and the λ cI857-pR inducible promoter system was inserted into the unique SalI site in the kanamycin resistance (aphA+) fragment of pML31 (D. R. Helinski, *J. Bact.* 127, 1976, pp. 982–987) by blunt end ligation (S1 nuclease was used to make the restricted DNA fragments blunt-ended).

The R1 derived translational fusion vector pJEL124 (shown in FIG. 14), which contains a polylinker in front of the lacZ gene lacking the first 7⅓ codon (lacZ') was used for all translational fusions between the hok gene and the lacZ gene. The copy number of the R1 based transcriptional and translational fusion vectors used herein is approximately 1 per *E. coli* genome.

Plasmids pKG733 and pKG732: pKG733 was constructed by inserting the BamHI-Sau3A restriction fragment of pPR633 (+1 to +342) into the BamHI site of pJEL124. The Sau3A site at +342 is located within the hok gene and positioned so that fusion of lacZ to this site creates a hybrid reading frame consisting of the first 14 amino acids of the hok gene followed by the lacZ' coding region. Thus, expression of β-galactosidase activity from the translational fusion plasmid pKG733 is controlled by signals normally controlling the expression of the hok gene. Plasmid pKG732 was constructed by inserting a 190 bp EcoRI-BamHI fragment of pSKS106 containing the lacUV5 promoter in front of the parB derived insert of pKG733.

Plasmids pKH734 and pKG735: pKG734 was constructed by inserting the BamHI-Sau3A fragment of pPR634 (+194 to +342) into the BamHI site of pJEL124. Plasmid pKG735 was constructed by inserting the 190 bp EcoRI-BamHI fragment of pSKS106 containing the lacUV5 promoter in front of the parB derived insert of pKG734.

Plasmids pKG741 and pKG742: pKG741 was constructed by inserting the BamHI-Sau3A fragment of pPR341 (+268 to +342) into the BamHI site of pJEL124. Plasmid pKG742 was constructed by inserting the 190 bp EcoRI-BamHI fragment of pSKS106 in front of the parB derived insert of pKG741.

Plasmids pKG780 and pKG782: A BamHI-BclI restriction fragment of pKG733 encoding the sok gene and the hok' gene fused in frame to the lacZ' gene was inserted in the two possible orientations into the BamHI site of pPR345, a pBR322 plasmid derivative containing the parB region extending from +350 to +580 on a BamHI-EcoRI restriction fragment (FIG. 7).

Promoter fusion plasmids: In all the promoter fusion constructs between the hok and sok promoters and the lacZ gene the R1 based transcriptional fusion vector pJEL126 (see FIG. 14) which contains EcoRI and BamHI restriction sites in front of the intact lacZ gene was used.

Plasmids pKG730 and pKG736: The EcoRI restriction fragments of pKG732 and pKG735 were inserted into the EcoRI site of pJEL126, resulting in pKG730 and pKG736, respectively.

Plasmid pUC341: The BamHI-EcoRI restriction fragment (+268 to +580) of pPR341 was replaced by the small EcoRI-BamHI restriction fragment in front of the lacZ gene of pJEL126, resulting in pUC341.

Microbiological methods

Partitioning test I: The construction of Lac$^+$ vectors made it possible to determine the Par$^+$ phenotype of a plasmid simply by streaking on nonselective McConkey lactose plates or X-Gal plates. Bacteria (Δ lac) harbouring these plasmids mediate a Lac$^+$ phenotype easily scored as coloured colonies on the indicator plates, while plasmid-free cells have a Lac$^-$ phenotype and appear as colourless colonies.

Partitioning test II: (Used for Lac$^-$ plasmids): A colony from a selective plate (a plate containing an antibiotic) was streaked on another selective plate. From this plate, one colony was streaked on an LA plate so as to form single colonies. From the LA plate approximately 10 colonies were suspended in 1 ml of 0.9% of NaCl to a dilution of $10^{-4}$ and $10^{-5}$, respectively 0.1 ml of the $10^{-4}$ and $10^{-5}$ dilutions were spread on LA plates. From these plates, the resistance pattern of 50 colonies (200 colonies if a weak instability is expected) were tested on the appropiate selective plates. The frequency of loss (LF value) is then calculated on the basis of the formula $$LF=1-(v)^{(1/27)}$$

where v is the frequency of plasmid-bearing cells and assuming that one colony grows for 27 generations. Inherent in this method is a large statistical fluctuation.

Partitioning test III: Quantitative measurements of the stability of Lac$^+$ and Lac$^-$ plasmids. One complete colony was taken from a selective plate and resuspended in 1 ml of 0.9% of NaCl to a concentration of $10^8$ cells/ml. 2×0.1 ml of the $10^{-3}$ dilution were used to inoculate 2×10 ml of LB medium and inoculation was performed at 30° C. with shaking. At a cell density of about $5×10^8$ cells/ml, the cultures were diluted $10^4$ and $10^5$ fold. 0.1 ml of the $10^4$ dilution ($5×10^3$ cells) was used to inoculate 10 ml of fresh LB medium and 0.4 ml of the $10^5$ dilution was spread on McConkey lactose plates, and the plates were inoculated at 30° C. overnight. The dilution from $5×10^8$/ml to $5×10^2$/ml corresponds to 20 generations of growth ($2^{20}$), so the change in the frequency of plasmid bearing cells from one dilution to the next corresponds to that occurring during 20 generations of growth. More generally, the LF value can be calculated as follows:

$$v_1=(1-LF)^{g_1} \text{ and } v_2=(1-LF)^{g_2}$$

where $v_1$ and $v_2$ are the frequency of plasmid bearing cells after $g_1$ and $g_2$ generations, repectively and LF is the frequency of loss per cell per generation. Hence, it follows that $$v_1/v_2=(1-LF)^{g_1-g_2}$$

and $$LF=1-(v_1/v_2)^{(1/(g_1-g_2))}$$

Using this formula, errors because of fluctuations in the number of inoculating cells at time zero are avoided. A more convenient approximation of this formula is $$LF=ln(v_1/v_2)/(g_2-g_1)$$

Incompatibility test

Plasmids believed to carry an inserted par region were screened for by utilizing the observation that two otherwise compatible replicons carrying the same par region are incompatible with one another, leading to the loss of either of the two in the absence of selection pressure. The test is performed by transforming the plasmid to be tested to a bacterial strain carrying another plasmid, selecting for both plasmids on double selective plates. After streaking on a double selective plate (a plate containing two different antibiotics), the incompatibility was measured either qualitatively or quantitatively.

For the qualitative incompatibility test, a colony from the double selective plate was streaked on an LA plate to form single colonies. About 10 colonies from this plate were resuspended in 1 ml of 0.9% NaCl and diluted to $10^{-4}$ and $10^{-5}$, respectively 0.1 ml of the $10^{-4}$ and $10^{-5}$ dilutions were spread on LA plates. From these plates, 50 colonies (or 200 colonies if a weak incompatibility was expected) were tested on the appropiate selective plates. If a Lac$^+$ plasmid was included in the test, McConkey lactose indicator plates were used instead of replica plating on selective plates. In the case of Lac$^+$ plasmids, the screening was thus performed by transforming suspected Par$^+$ plasmids to a strain already harbouring a Par$^+$ hybrid plasmid mediating a Lac$^+$ phenotype. Plasmid incompatibility, and consequently proof of a specific Par$^+$ phenotype of the incoming plasmid is easily detected by screening for Lac$^-$ colonies on McConkey plates, showing that the resident Par$^+$ plasmid had been destabilized. An example of this screening procedure is described in Example 4.

Quantitative incompatibility measurements were carried out by measuring the loss frequencies of Lac$^+$ plasmids after establishing heretoplasmid populations as described above. The LF values were measured as described under "Partitioning test III".

Purification of chromosomal DNA

Total DNA was extracted from bacteria as follows. Cells were harvested by centrifugation, washed twice in 1×TEN buffer (TEN=10 mM TRIS (pH 7.5), 1 mM EDTA, 0.1M NaCl) and resuspended in 1/10th volume of TEN containing 1 mg/ml lysozyme. Following incubation at 37° C. for 30 minutes, the protoplasts were lysed by addition of sodium dodecyl sulphate to a final concentration of 1%, and proteinase K was added to 0.25 mg/ml. The lysate was incubated at 37° C. for 2 hrs and subsequently extracted twice with buffered phenol and three times with chloroform. Sodium acetate was added to 0.3M and the DNA was precipitated by addition of 1 volume isopropanol. The precipitate was washed several times in 96% and 80% ethanol. Finally, the DNA was dissolved in 1 mM TRIS, 1 mM EDTA.

Total DNA from *Tetrahymena thermophila* BVII was prepared according to Nielsen, H. and Engberg, J.: *Biochim. Biophys. Acta* 825, 1985, pp. 30–38. Macronuclei from *Tetrahymena thermophila* BVII were isolated (Cech, T. R. et al: *Cell* 27, 1981, pp. 487–496) and DNA extracted (Maniatis et al., 1982, op. cit., pp. 280–281). rDNA from *Tetrahymena thermophila* BVII was prepared as described by Engberg, J. et al.: *J. Mol. Biol.* 104, 1976, pp. 455–470.

Chloroplast DNA from *Pisum sativum* was isolated according to Bookjans, G. et al.: *Analyt. Biochem.* 141, 1984, pp. 244–247.

Embryonic liver tissue from a 7-weeks legal abortion was minced in physiological saline and the DNA was prepared according to Maniatis et al., 1982, op. cit., pp. 280–281. In a similar manner, DNA was isolated from a tumor biopsy from a case of neuroblastoma; the isolated DNA was found to contain a several hundred-fold amplified chromosomal region and, correspondingly, the tumor cells were found to contain numerous extrachromosomal mini-chromosomes by microscopy of mitotic cells.

Isolation of DNA fragments for radioactive labelling 100 micrograms of pPR95 and pBD2724 DNA were digested with EcoRI and EcoRI and HindIII, respectively. The fragments were separated by electrophoresis through a 1% agarose gel in Tris-borate buffer at 5 volts per cm for 3 hours. The desired fragments were isolated by electroelution onto an NA45 membrane (Schleicher & Schüll) according to the manufacturer's recommendations. Following recovery of the fragments by elution of the filter in 1.5M NaCl at 65° C., the fragments were again subjected to purification by agarose gel electrophoresis and NA45 membrane recovery from the gel.

Agarose gel electrophoresis

The DNA was cleaved with the appropriate restriction endonucleases according to the recommendations given by the manufacturers. For cellular DNA, 10 units per microgram of DNA was used. The incubation time was 3 hours at 37° C. The generated DNA fragments were separated by electrophoresis through 0.7% or 1% agarose gels in a Tris-acetate buffer at 0.8 volt per cm for 18 hours and visualized by ethidium bromide staining.

A molecular weight marker was prepared as follows: wt λ DNA was restricted with HindIII and end-labelled by means of the Klenow polymerase from Boehringer, Mannheim, as recommended by the manufacturer, in the presence of α-32P-dCTP plus non-radioactive dATP and dGTP. When used as a molecular weight marker, an amount of Tetrahymena macronuclear DNA was added corresponding to the DNA load of the test lanes.

Transfer of DNA fragments from gel to nitrocellulose filter

Following partial depurination in 0.25N HCl for 15 minutes at room temperature, denaturation of DNA in the gel, neutralization and subsequent transfer of DNA from gel to a BA85 (Schleicher & Schüll) nitrocellulose filter was carried out as described in Maniatis et al., 1982, op. cit., pp. 280–281. Completeness of transfer was assured by ethidium bromide staining of the gel after transfer.

Preparation of radioactively labelled probe 0.3 microgram of the 900 bp parB fragment and 0.3 microgram of the 300 bp relB-orf3 fragment were radioactively labelled by nick-translation (Maniatis et al., 1982, op. cit.) using 0.25 micromolar α-32P-deoxycytidine triphosphate (3000 Ci per mmol). The unincorporated radioactive precursor was removed by means of repeated ethanol precipitations.

To each preparation were added 100 micrograms of *E. coli* tRNA as carrier.

The specific activities of the probes were 2–3×10$^8$ and 4–5×10$^7$ dpm per microgram of parB and relB-orf3 fragment, respectively.

Hybridization

Filters containing DNA transferred from agarose gels were preincubated in plastic bags with the hybridization solution (10 ml per 120 cm$^2$) for 18 hours at 37° C. with constant shaking. The hybridization solution was modified from Wahl et al., *Proc. Natl. Acad. Sci.* 76, 1979, pp. 3683–3687 and contained 38% deionized formamide, 0.75M NaCl, 50 mM sodium phosphate and 10×Denhardt's solution (50×Denhardt's solution is 0.2% bovine serum albumin, 0.2% polyvinylpyrrolidone and 0.2% Ficoll).

Following preincubation, the denatured radioactively labelled probes were added to appropriate filters. In experiments employing the parB probe, the concentration of fragment during hybridization was 3 ng/ml while the relB-orf3 probe was used at a concentration of 1.3 ng/ml to obtain equimolar concentrations of complementary sequences in the two situations.

Hybridization was carried out at 37° C. with gentle shaking for 19 hours.

The hybridized filters were washed once for 20 minutes at room temperature in 0.4×washing buffer, and finally twice for 30 minutes at 60° C. in 4×washing buffer. The washing buffer contained 0.6M NaCl, 0.1% SDS, 0.1% sodium pyrophosphate, 50 mM sodium phosphate, pH 6.5. Autoradiography was performed using X-ray films and intensifying screens. Exposure times are indicated in the description of the figures.

The term "filter hybridization analysis" is used in the Examples to denote the following sequence of operations: agarose gel electrophoresis of DNA fragments, transfer of the fragments to nitrocellulose filters, hybridization with the appropriate radioactively labelled probe, filter washing, and autoradiography of the filter following washing. The data shown in the Examples represent autoradiograms obtained by filter hybridization analysis.

The term homology is used here to denote the presence of any degree of complementarity between a given probe and the nucleic acid species being analyzed.

The degree of homology is expressed as the fraction of complementary bases in a duplex nucleic acid molecule formed between a given probe and the nucleic acid species being analyzed.

The minimum degree of homology which is detectable is a function of the experimental conditions exployed during hybridization and of characteristics of the probe and the nucleic acid species being analyzed.

The degree of homology between the probe DNA and a filter-bound DNA species was estimated from the intensity of the actual hybridization signal compared to the signal intensity observed for a 100% homologous filter-bound sequence under the same conditions.

The intensity of the hybridization signal depends primarily on the rate of hybridization and the number of filter-bound DNA molecules present in the specifically hybridizing band. The rate of hybridization is mainly determined by the concentration of complementary sequences during hybridization, the ionic conditions, the temperature and the degree of homology between the probe DNA and the filter-bound molecules. The rate of hybridization decreases by the presence of non-complementary sequences (Bonner, T. I. et al., *J. Mol. Biol.* 81, 1973, p. 123) which decreases the thermal stability of the duplex DNA; 1% mismatch between probe and filter-bound DNA results in a decrease in thermal stability of 1 degree (Maniatis et al., 1982, op. cit., p. 388). The hybridization conditions therefore determine which level of mismatch will still yield a detectable signal. It should be noted that the conditions employed in the present work did not lead to saturation of the filter-bound DNA with probe.

The present set of conditions for hybridization and filter subjects DNA duplexes to a temperature which is 40° C. below the mean melting temperature of perfectly matched duplex DNA in the same ionic environment, i.e. the conditions allow the detection of signals from duplexes containing a high degree of non-pairing bases. The formula used in these calculations is discussed in Beltz, G. A. et al., *Meth. Enzymol.* 100, 1983, pp. 266–285.

It is estimated that the conditions employed detect 100% of the maximum hybridization signal obtained from duplexes with from 100% down to 80% homology while the signal from a 60% homologous duplex is 50% of the above maximum intensity, cf. above. Duplexes with lower homology than 60% will yield still weaker signals.

For duplexes with extensive mismatch, a signal may be detectable if the exposure time of the autoradiogram can be prolonged or if the number of copies of filter-bound complementary molecules can be increased.

TABLE 1

Plasmids

| Plasmid | Type of replicon | parB phenotype (where relevant) | Relevant Genotype | Coordinates of parB insert (cf. FIG. 1) | Incompatibility* group |
|---|---|---|---|---|---|
| R1drd-19 | | + | | | FII |
| R100 | | + | | | FII |
| R386 | | + | | | FI |
| RP1 | | | | | P |
| R6-K | | | | | X |
| pML31 | F | | | | FI |
| pPR95 | R1 | + | (hok+, sok+) | −300 - +580 | |
| pPR311 | R1 | + | (hok+, sok+) | −300 - +580 | |
| pPR633 | pBR322 | + | (hok+, sok+) | +1 - +580 | |
| pPR634 | pBR322 | − | (hok+ | +194 - +580 | |
| pPR341 | pBR322 | − | (hok+) | +268 - +580 | |
| pPR171 | pBR322 | − | | −300 - +288 | |
| pPR154 | pBR322 | − | (sok+) | −300 - +330 | |
| pKG633 | pBR322 | + | (sok+, hok+) | +1 - +580 | |
| pKG634 | pBR322 | − | (hok+) | −194 - +580 | |
| pKG341 | pBR322 | − | (hok+) | +268 - +580 | |
| pKG171 | pBR322 | − | | −300 - +288 | |
| pBD2724 | pBR322 | | relB−orf3 | | |
| pF634 | F | − | (hok+) | +194 - +580 | |
| pFN13 | p15 | + | (hok+, sok+) | −300 - +580 | |
| pOU94 | p15 | + | (hok+, sok+) | −1100 - +760 | |
| pJEL124 | R1 | | | | |
| pJEL126 | R1 | | | | |
| pSKS106 | pMB1 | | | | |
| pBR322 | pMB1 | | | | |
| pHB4 | pMB1 | | | | |
| pPR13 | pMB1 | | | −300 - +580 | |
| pPR341 | pMB1 | | (sok−) | +268 - +580 | |
| pPR345 | pMB1 | | (hok−, sok−) | +350 - +580 | |
| pPR437 | R1 | | (hok+, sok+) | +1 - +580 | |
| pPR438 | R1 | | (hok+, sok'+) | +194 - +580 | |
| pUC341 | R1 | | (sok−) | +268 - +580 | |
| pKG730 | R1 | | (sok+) | +1 - +342 | |
| pKG732 | R1 | | (hok'−lacZ+, sok+) | +1 - +342 | |
| pKG733 | R1 | | (hok'−lacZ+, sok'+) | +1 - +342 | |
| pKG734 | R1 | | (hok'−lacZ+, sok'+) | +194 - +342 | |

TABLE 1-continued

| Plasmid | Type of replicon | parB phenotype (where relevant) | Relevant Genotype | Coordinates of parB insert (cf. FIG. 1) | Incompatibility* group |
|---|---|---|---|---|---|
| pKG735 | R1 | | (hok'–lacZ+, sok+) | +194 - +342 | |
| pKG736 | R1 | | (sok+) | +194 - +342 | |
| pKG741 | R1 | | (hok'–lacZ+) | +268 - +342 | |
| pKG742 | R1 | | (sok') | +268 - +342 | |
| pKG780 | pMB1 | | (hok'–lacZ+, sok+) | +1 - +342 | |
| pKG782 | pMB1 | | (hok'–lacZ+, sok+) | +1 - +342 | |
| PSI-1 | pUB110 pMB1 | | | | |
| pJK3-1 | pBC16 pMB1 | | | | |

EXAMPLE 1

Figure 2:
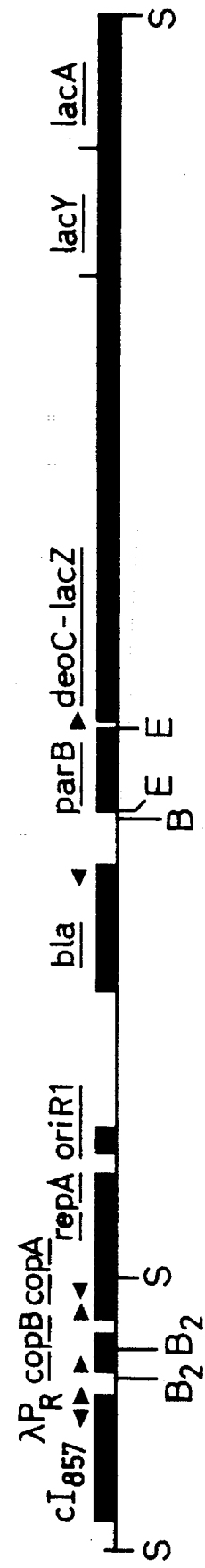
FIG. 2 shows a map of plasmid pPR95 (13 kb). copA, copB represents replication control genes of plasmid R1; repA represents a gene required for R1 replication; ori is the origin of replication; bla denotes a gene conferring ampicillin resistance on plasmid-carrying cells; parB represents the R1 derived region comprising the hok and sok genes expressing a maintenance function; deoC-lacZ' denotes a translational fusion between the deoC gene and the lacZ gene. lacZ,Y,A represents the lac operon; cI857 represents a gene which codes for a temperature-sensitive λ repressor controlling λpR promoter activity. Arrows denote the direction of transcription. The black bars denote the extension of the various genes. Restriction enzyme sites are shown as S (SalI), $B_2$ (BglII), B (BamHI) and E (EcoRI).

Deletion mapping of the parB region (cf. FIG. 1)
Construction of pPR95 (FIG. 2)

The construction of pPR95 was done in the following way: plasmid pOU93 (Gerdes et al., *J. Bacteriol.* 161, 1985, pp. 292–98) is a pBR322 derivative containing the parB PstI fragment derived from the EcoRI-A fragment of plasmid R1 (FIG. 1). The PstI fragment is conveniently divided into smaller fragments by the restriction enzyme RsaI as shown in FIG. 1. By conventional cloning procedures, the largest RsaI fragment (880 bp) was inserted into the SmaI site of the pBR322 derived cloning vector pHP34 (Prentki et al., *Gene* 17, 1982, pp. 189–96), resulting in pPR13. The SmaI site of pHP34 is flanked by two EcoRI sites and therefore the inserted 880 bp RsaI fragment was converted to a 900 bp EcoRI fragment. The so generated 900 bp EcoRI fragment of pPR13 was cloned into the unique EcoRI site of the miniR1 derivative pOU82 (International Patent Application No. PCT/DK83/00086, Publication No. WO 84/01172, now U.S. Pat. No. 4,760,022, and International Patent Application No. PCT/DK83/00084, Publication No. WO 84/01171, new U.S. Pat. No. 4,806,471), resulting in pPR95. A drawing of pPR95 is presented in FIG. 2. Plasmid pOU82 is unstably inherited due to the lack of any partitioning function (International Patent Application No. PCT/DK83/00086, Publication No. WO 84/01172) now U.S. Pat. No. 4,760,022, and has a loss frequency on the order of $10^{-2}$ per cell per generation.

On the other hand, pPR95 is very rarely lost, and is characterized by having a loss frequency of less than $10^{-4}$ per cell per generation (measured as described in International Patent Application No. PCT/DK 83/00086, Publication No. WO 84/01172), which is the characteristic loss frequency of parB+ miniR1 derivatives. Thus, it may be concluded that the complete parB region is located on the 880 bp RsaI fragment as judged by the ability of the fragment to stabilize miniR1 replicons.

The fine mapping of the parB region was carried out as follows: pPR95 was restricted with BamHI, treated with exonuclease Bal31, and ligated. Before ligation, BamHI oligonucleotide linkers were added. This treatment resulted in a series of deletion derivatives covering the left-hand part of the parB region. The extension of the deletions was determined by size fractionation of DNA fragments on agarose gels after the DNA had been treated with the restriction enzymes EcoRI and BamHI. Subsequently, the precise insertion of the BamHI oligonucleotide linkers was determined by nucleotide sequencing as described by Maxam and Gilbert (*Meth. Enzymol.* 65, 1980, pp. 499–566). In this way, a very detailed mapping of the region was obtained. Furthermore, the ParB phenotype (determined as described in Materials and Methods) for each plasmid derivative was analyzed. Deletion from pPR95 of the sequence extending from –320 to 0 (cf. FIG. 1) resulting in pPR311 did not change the ParB+ phenotype. Thus, the remaining 580 bp BamHI-EcoRI fragment in pPR311 must contain the complete parB region. Deletion from left further into the region completely abolishes the stabilizing activity.

Deletions into the right part of the 580 bp parB fragment of pPR311 (cf. FIG. 1) resulted in loss of ParB+ phenoptype, so the parB region extends to a position close to this end of the fragment.

EXAMPLE 2

Nucleotide sequence of the parB region (cf. FIG. 3)

The nucleotide sequence of the minimal parB region, which is presented in FIG. 3, was obtained using the chemical degradation method as described by Maxam and Gilbert (*Meth. Enzymol.* 65, 1980, pp. 499–566). In the following, a detailed description of the essential biological information in the nucleotide sequence of the parB region is presented.

The sequence of the minimal parB region of 580 bp as defined in Example 1 (cf. FIG. 1) is depicted in FIG. 3. The central and right hand parts of the region are very rich in dyad symmetries. The 580 bp contains three open reading frames consisting of more than 50 codons. The start and stop codons of these reading frames are indicated in FIG. 3. The reading frame starting at position +304 and ending at +460 is preceded by a DNA sequence (5'-AGGA-3') resembling the *E. coli* ribosome binding site (Shine and Dalgarno, *Nature* (London) 254, 1975, pp. 34–38), which is known to act as recognition site for ribosomes initiating translation of mRNA. The polypeptide product of this reading frame is shown below the DNA sequence in FIG. 3.

EXAMPLE 3

Figure 4:
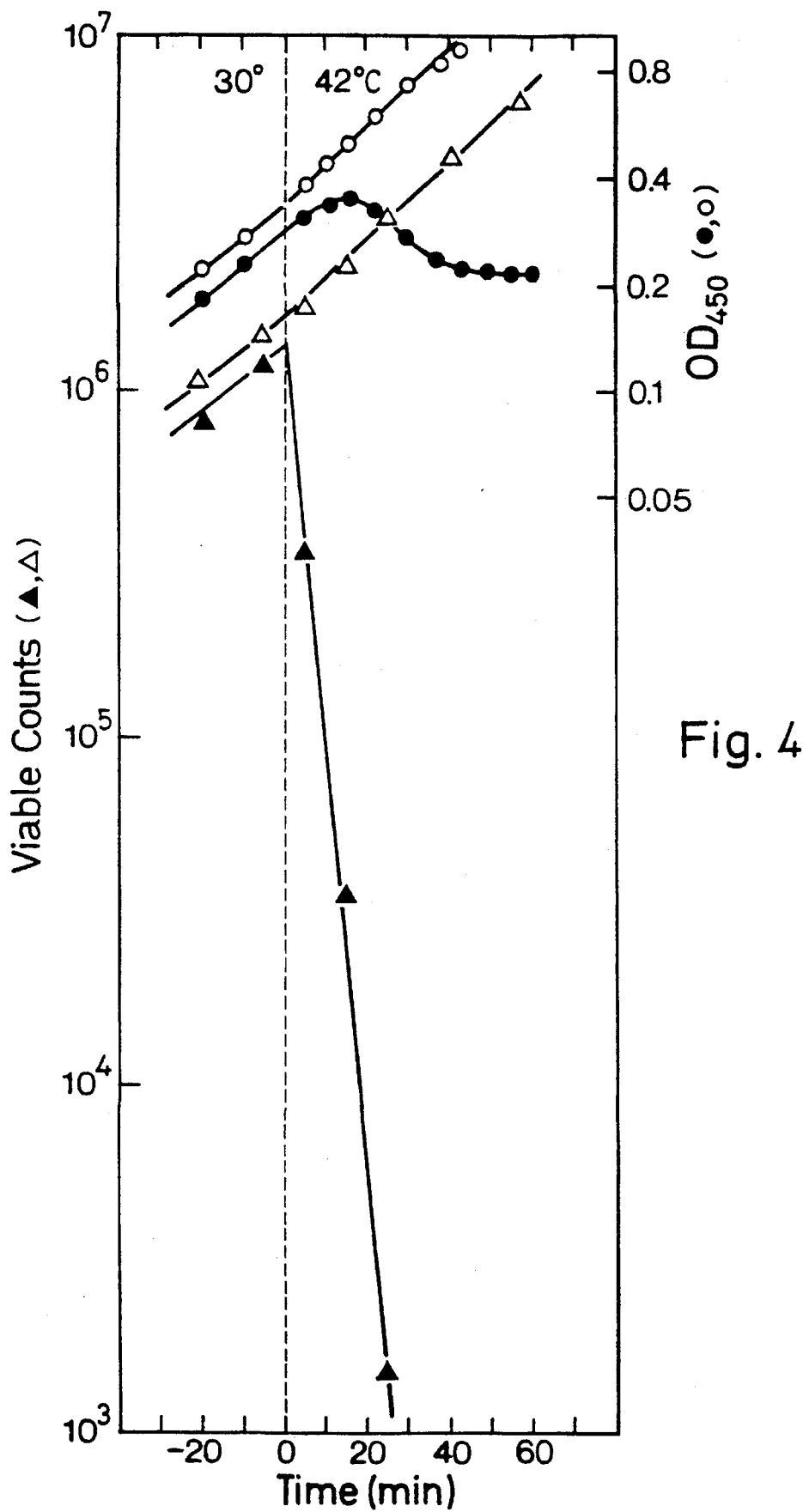
FIG. 4 shows host cell killing after λpR induced activation of the hok gene. Strain JC411 containing either pKG634 (filled-in symbols) or pKG171 (open symbols) was grown exponentially in A+B minimal medium supplemented with casamino acids at 30° C. At time zero, the temperature was shifted to 42° C. and growth of the cultures was followed as $OD_{450}$ and viable counts on selective medium (LB plates containing 50 µg/ml ampicillin).
Figure 5:
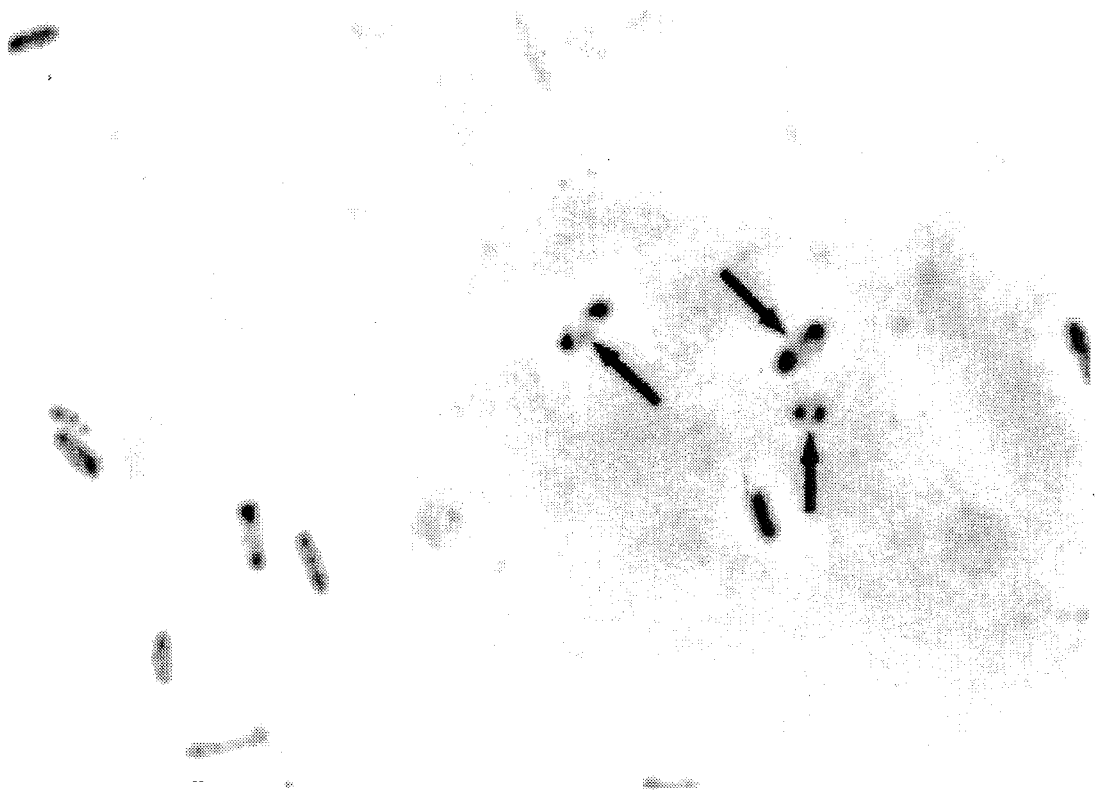
FIG. 5 is a photograph of cells sampled 1 hour after the shift of strain JC411 (pKG634) to 42° C. The arrows point at cells with a clearly changed morphology. Cells with a normal morphology are also seen. Magnification×2000.

Functions expressed from the parB region (cf. FIGS. 4 and 5)

A series of plasmids was constructed from which conditional expression of the putative genes (as indicated from the sequence) in the parB region was obtained through insertion of a fragment carrying the λpR promoter and the λcI857 gene. The positions of these insertions are indicated in FIG. 1. The λpR temperature inducible promoter system was chosen because the regulator gene for the λpR promoter (the cI857 gene) as well as λpR are located on a single BglII-SalI restriction fragment; furthermore, the cI857 allele of the λ repressor gene makes the inserted promoter inducible at high temperature (42° C.), but silent or near silent at low temperature (30° C.). The BglII-SalI fragment of pOU82 was inserted into plasmids pPR634 and pPR341 by conventional cloning procedures yielding plasmids pKG634 and pKG341, respectively (cf. Materials and Methods).

At 30° C., cells harbouring pKG634 and pKG341 grow normally; however, induction of λpR (at 42° C.) results in rapid killing of the host cells.

FIG. 4 shows the killing kinetics (viable counts) and growth measured as OD450 after a shift to 42° C. of strain JC411 (pKG634). Viable counts decrease rapidly (half life of 2.5 minutes) and the increase of OD450 stops. The presence of a λpR promoter transcribing the parB region in the opposite direction (pKG171) has no effect on cell growth and viability (FIG. 4, control).

Microscopic examination (phase contrast) of the cells (JC411/pKG634) after heat induction of the λPR promoter showed that the cells changed morphology: Most of the material apparently condensed in zones, leaving the rest of the cell transparent. An illustration of this is shown in FIG. 5, in which both normal and changed cells are present. The cells having the characteristic parB-induced appearance are termed "ghost" cells in the following.

Since the λpR-promoter fragment was inserted immediately upstream of the start of a 52 amino acids open reading frame (cf. Example 2), this strongly suggests that the 52 amino acids polypeptide encoded by the open reading frame starting at position +304 (FIG. 3) is responsible for the cell killing, and consequently, this gene is termed hok (host killing) in the following.

EXAMPLE 4

Figure 6:
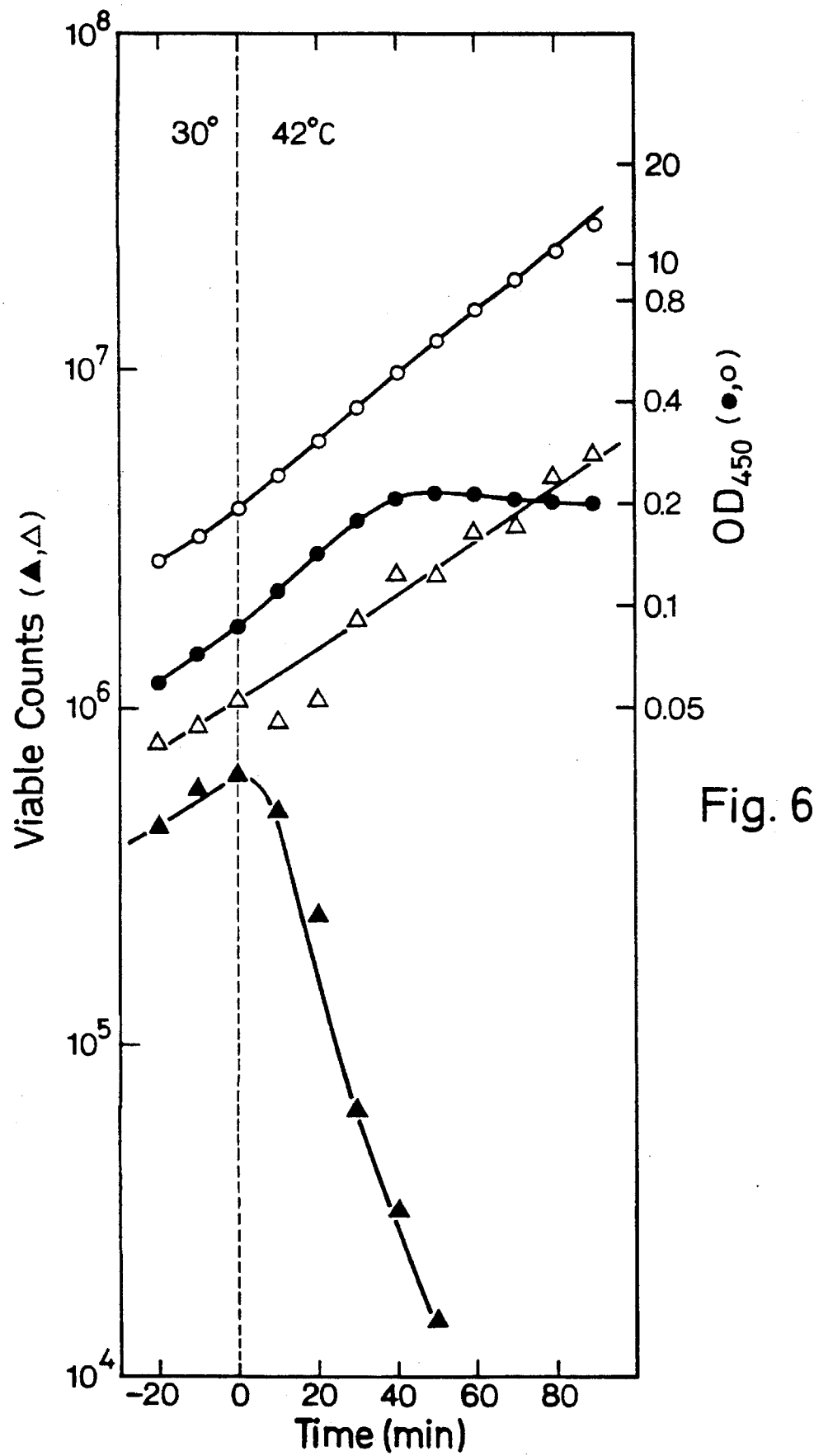
FIG. 6 shows the suppression of host cell killing. Strain JC411 containing either pF634 alone (filled-in symbols) or pF634 plus pPR633 (open symbols) was grown exponentially in A+B minimal medium supplemented with casamino acids at 30° C. At time zero, the temperature was shifted to 42° C. and growth of the cultures was followed by measuring the optical density ($OD_{450}$) and viable counts on selective medium (LB plates containing 100 µg/ml kanamycin).

Suppression of the host killing effect expressed by hok (cf. FIG. 6)

A gene from which a highly toxic product is expressed must obviously be regulated. Therefore, it was assumed that the regulator of hok was also encoded by the parB region. In a first attempt to characterize this regulatory loop, the fragment of pKG634 containing λcI857 upstream of the hok gene was inserted into a mini-F plasmid, resulting in pF634. FIG. 6 represents the induction of killing of JC411 (pF634) which shows that the killing occurs somewhat slower and less efficiently than in the case of pKG634 in accordance with the low copy number of F compared to pBR322.

A second parB$^+$ plasmid (pPR633) was subsequently transformed into strain JC411 (pF634) and the induction experiment repeated with this double plasmid strain. As seen in FIG. 6, the parB region present in trans fully suppresses the transcriptional activation of the hok gene. Thus, the parB region encodes a suppressor of host killing (the sok gene).

Employing this experimental design as an assay, the sok gene was mapped in the following way: Double plasmid strains containing pF634 and one of the deletion derivatives pPR634, pPR341, pPR154, or pPR171, respectively, were constructed, and by following the growth pattern of these strains at 42° C., the Sok phenotype of the deletion derivatives was determined by measuring growth after the temperature shift. The analysis of these deletion derivatives showed that the plasmids pPR634 and pPR154 express Sok activity, whereas the plasmids pPR341 and pPR171 express non-detectable levels of Sok activity.

The plasmids were also tested for the incompatibility phenotype characteristic for parB$^+$, (cf. International Patent Application No. PCT/DK 83/00086, Publication No. WO 84/01172), and it was found that plasmids expressing Sok activity also exert parB specific incompatibility, whereas plasmids which are Sok$^-$ as described above do not exert incompatibility. Thus, the parB incompatibility reaction represents an assay for Sok activity.

In a manner similar to that described for the hok gene, the region required for sok gene activity has been further narrowed down. One of the sok$^-$ derivatives used in the mapping procedure, pPR171, contains the parB region extending from coordinate $-300$ to $+288$ (FIGS. 1 and 3). A restriction fragment containing the λcI857 and λpR was inserted into pPR171 in such a way that the λpR promoter reads into the sok region of the plasmid, resulting in pKG171 (cf. Materials and Methods).

Plasmid pKG171 was transformed to strain CSH50 containing pOU94. Plasmid pOU94 is a lac$^+$ parB$^+$ p15 derivative which is completely stably inherited due to the presence of the parB region on the plasmid. Introduction of other parB$^+$ plasmids into that strain results in destabilization of pOU94 due to the incompatibility expressed from parB. At 30° C., the presence of pKG171 did not result in destabilization of pOU94 to any significant extent, whereas a clear destabilization was detected at 42° C. Therefore, transcription from right to left into the parB region of pKG171 results in activation of the incB region (i.e., the sok gene).

The results described here further narrows down the sok gene which must therefore be located between $+194$ (pPR634) and $+288$ (pPR171). Also, it is indicated that the sok gene promoter reads from right to left (opposite of hok gene transcription) and is located at least partly in the region between $+288$ (pPR171) and $+336$ (pPR154). A putative $-10$ sequence (TATCCT) is located at position $+262$ and a $-35$ sequence (TTGCGC) is located at position $+285$ (FIG. 3) (Hawley and McClure, *Nucleic Acids Res.* 11, 1983, pp. 2237–2255). It is assumed that these sequences constitute the promoter of the sok gene.

EXAMPLE 5

Figure 14A:
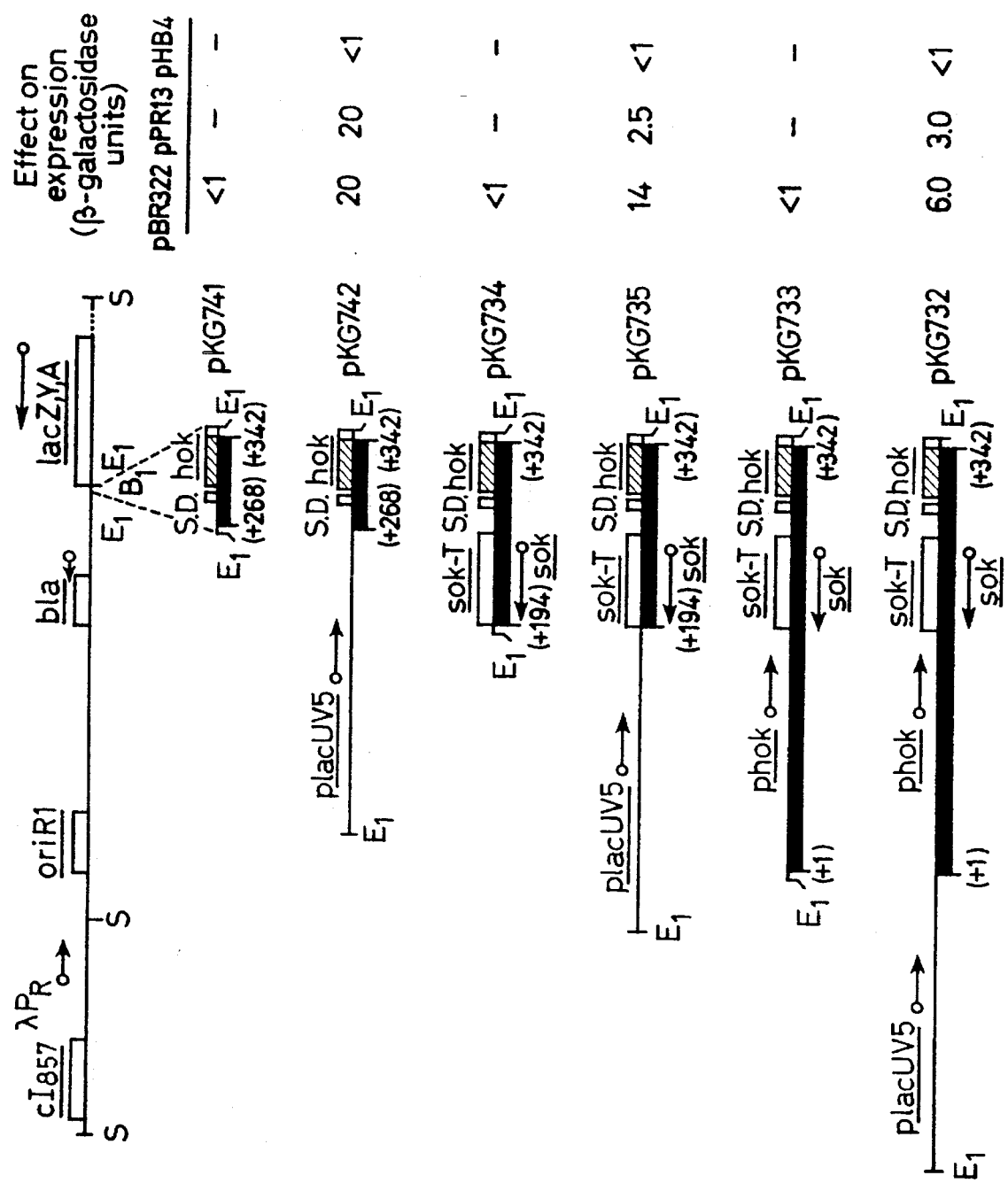
FIGS. 14A and 14B show restriction maps of translational and transcriptional fusion vectors based on pJEL124(A) and pJEL126(B). The latter plasmid differs from pJEL124 in that it comprises the Shine-Dalgarno sequence of the lacZ gene. In the figure, cI857 denotes the gene for a temperature sensitive repressor controlling λpR promoter activities, oriR1 denotes the origin of replication, bla denotes a gene conferring ampicillin resistance on plasmid-carrying cells, lacZ, Y, A denotes the lac operon, S.D. with an open box denotes a Shine-Dalgarno sequence, phok denotes the hok promoter and placUV5 denotes the lac promoter region. The arrows show the direction of transcription, the black bars indicate the extent of the insert from the parB region, the hatched bars denote the hok gene or a part thereof, the open bars denote the sok gene or a part thereof, sokT denotes the target of the Sok gene products and restriction enzyme sites are shown as $E_1$ (EcoR1), $B_1$ (BamHI) and S(SalI). The columns to the right show the β-galactosidase activities expressed from the fusion plasmids when the plasmids pBR322, pPR13 (pBR322-parB+,sok+,hok+), or pHB4 (pBR322-lac+) are also present in the host cells.
Figure 14B:
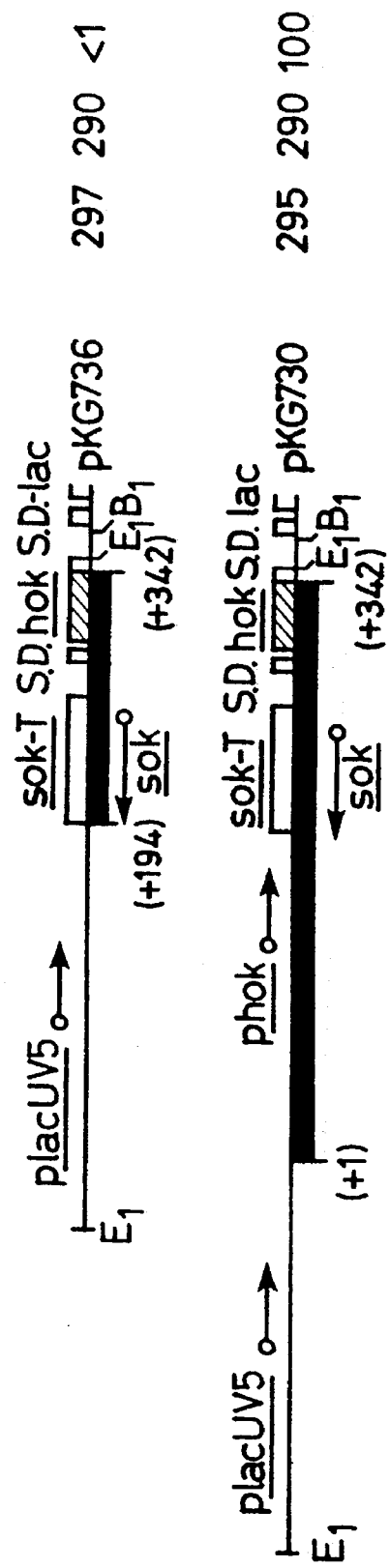

Further analysis of the hok and sok gene structure and the interaction between the hok and sok transcripts Regulation of hok gene expression at the translational level by the Sok gene product In order to gain further insight into the regulatory loop controlling the expression of the hok gene, a series of translational and transcriptional fusions between the hok gene and the lacZ gene were constructed (cf. FIG. 14). The β-galactosidase activities expressed from the translational fusion plasmids pKG733, pKG734 and pKG741 were very low, below one unit (as defined in Materials and Methods). Activities that low cannot be accurately measured, and therefore a DNA fragment encoding the regulatable lac promoter was inserted into pKG733, pKG734, and pKG741 upstream of the DNA fragments derived from the parB region, resulting in pKG732, pKG735, and pKG742, respectively. These plasmids express low, but measurable amounts of β-galactosidase.

Plasmids pBR322 and pPR13 (pBR322parB$^+$) were separately transformed to strain CSH50 containing the translational fusion plasmids pKG732 (parB derived insert from +1 to +342) or pKG735 (parB insert from +194 to +342). The parB region present in trans was shown to reduce the β-galactosidase activity expressed from the fusion plasmids from 6.0 to 3.0 units in the case of pKG732 and from 14.0 to 2.5 units in the case of pKG735. The same experiment was carried out with CSH50 carrying pKG730 and pKG736 which are transcriptional fusion plasmids carrying the same inserts as pKG732 and pKG735. No repression of the β-galactosidase synthesized from these plasmids was observed. It may therefore be concluded that the parB encoded repressor of hok gene expression (the sok gene product) acts as a post-transcriptional level, most likely at the level of translation (see below).

Genetic mapping of the sok gene

Derivatives of pBR322 carrying different segments of the parB region were transformed to CSH50 carrying pKG735, and the effect on the hok'-lacZ fusion protein synthesis was measured. Plasmids pPR633 (+1 to +580) and pBR634 (+194 to +580) repressed the hok'-lacZ synthesis from pKG735, whereas pPR341 ($^+$268 to +580) did not. Likewise, pPR154 (−300 to +336) repressed hok'-lacZ synthesis from pKG735, whereas pPR171 (−300 to +288) had no such effect. This indicates that an active repressor gene is located from +194 (pPR634) to +336 (pPR154). The mapping of the sok gene agrees with the mapping of the repressor gene using a functional assay of sok gene activity (described in Example 4).

Further characterization of the sok gene promoter

To measure the strength and direction of the sok promoter different Bal31 generated fragments derived from the parB region (Table 1) were inserted in front of the intact lacZ gene of the transcriptional fusion vector pJEL126. Plasmids pPR438 (fusion point +194) expressed high levels of β-galactosidase, whereas pPR341 (fusion point +268) did not express significant levels of activity, indicating that the sok gene promoter is not intact in PPR341. These results show that the sok pomoter is at least partly localized to the region between +194 and +268. Plasmid pPR437 (fusion point at +1) express an approximately 10 fold lower activity than pPR438 and therefore 90% of the sok gene transcripts must be concluded to terminate between +1 and +194.

A DNA fragment extending from the FokI site at +226 (labelled 5'-end) to the Sau961 site at +482 was hybridized to RNA prepared strain CSH50 containing pPR633 (pBR322-parB). After S1 nuclease treatment of the DNA-RNA hybrid, the sample was run on a denaturing sequencing gel together with Maxam-Gilbert reactions of the same DNA probe. A weak band appeared corresponding to a transcript starting at +258. This mapping of the 5'-end of the sok transcript agreed with the genetic mapping of the sok promoter described above.

The nucleotide sequence in the region upstream of +260 contains a putative −10 sequence (5'-TATCCT-3') located from +267 to +262 and a −35 sequence (5'-TTGCGC-3') located from +290 to +285 (bases conforming to the *E. coli* promoter consensus sequences according to Hawley and McClure (op.cit.), are in italics. Thus, all the information currently available, both genetic and physical, confirms the assumption of Example 4 that these sequences constitute the sok gene promoter. The transcription of β-galactosidase from the lac promoter (pKG736) gives a yield of about 300 units. The β-galactosidase transcribed from the sok promoter (pPR438) gives a yield of 1500 units. Thus, the sok promoter is a strong promoter with an activity which is approximately 5 times higher than that of the lac promoter.

The target of the sok gene product is located within the sok gene

The translational fusion plasmids shown in FIG. 14 were used to map the target of the Sok gene product (Sok-T). Addition of the sok gene in trans via pPR13 to pKG732 (insert from +1 to +342) and pKG735 (insert from +194 to +342) repressed the synthesis of the hok'-lacZ fusion proteins expressed by these plasmids, wereas no such effect was apparent in case of pKG742 (insert from +268 to +342; FIG. 14). Thus, the genetic target of the sok-RNA is concluded to be encoded by the DNA extending from +194 to +268, precisely overlapping the region encoding the sok-RNA itself. Plasmid pKG742 does not express the sok-RNA and this plasmid was expected to yield higher amounts of hok'-lacZ fusion protein than observed (see below).

S1 Nuclease mapping of the 5'-end and the 3'-end of the hok mRNA

An obvious promoter-like structure in the DNA sequence upstream of the hok gene coding frame is indicated in FIG. 3. This putative promoter, phok, has the −10 sequence (5'-TATGAT-3') and the −35 sequence (5'-TGGTCA-3') separated by 18 bp; no other obvious promoter-like sequences are found upstream of the hok gene coding region.

The 5'-end of the hok-gene transcript was identified by means of the S1 nuclease-based technique described in Materials and Methods. The probe used extended from the FokI site at +229 (labelled 5'-end) to the SfaNI site at +13. The probe was hybridized to RNA prepared from strain CSH50 containing pPR633 (pBR322-parB$^+$), treated with nuclease S1 and run on a polyacrylamide gel together with the Maxam and Gilbert reactions of the same DNA probe. Furthermore, the probe was also hybridized to RNA prepared from culture samples withdrawn at various times after adding rifampicin to the culture. Before rifampicin addition a very weak band appear corresponding to a transcript starting at +130 which corresponds to a transcript starting at +130 exactly in accordance with the promoter structure indicated by the DNA sequence. The addition of rifampicin resulted in a time-dependent enhancement of hybridization between the DNA probe and the RNA starting at +130: At 25 minutes after the addition of rifampicin the hybridization was several orders of magnitude more efficient than before addition of rifampicin. It is therefore believed that the major hok gene transcript starts at position +130. The rifampicin-induced time-dependent enhancement of hybridization between the transcript starting at +130 and the DNA probe used is thought to reflect the decay of an inhibitor of the hybridization reaction between the hok mRNA and the DNA probe. This inhibitor is most likely Sok-RNA, which is complementary to the same part of the hok mRNA as the DNA probe used. It should be noted that there was no inhibition of hybridization between the hok mRNA and a DNA probe complementary to the 3'-end of the hok mRNA.

The 3'-end of the hok mRNA was also mapped by the S1 nuclease technique. A DNA fragment extending from +342 (Sau3A site) to +580 (EcoRI site) was labelled in the 3'-end of the Sau3A site and hybridized to RNA prepared from CSH50 (pPR633), treated with S1 nuclease and run on a polyacrylamide gel together with the Maxam-Gilbert reactions of the DNA probe. The major part (80–90%) of the hok gene transcripts terminated at position +561, 562, and 563 and minor transcription termination points upstream of these positions were also observed. Position +561 is preceded by a potential stem-loop structure with a GC-rich stem followed by a run of U's bearing resemblance to typical rho independent transcription termination structures (Rosenberg and Court, *Ann. Rev. Genet.* 13, 1979, pp. 319–353).

Thus, the major hok gene transcript starts at +131/132 and terminates around +562.

The strength of the hok promoter was dermined by means of the transcriptional fusion plasmid pKG730 (FIG. 14), which contains the lac promoter and the hok promoters in tandem in front of the intact lacZ gene. The β-galactosidase activity expressed from pKG730 in CSH50 is about 300 units. To avoid transcription from the lac promoter, a pBR322 derivative carrying the loci gene (pHB4) was transformed to CSH50 (pKG730). This dual plasmid strain express a β-galactosidase level of 100 units (the lacI gene present in trans on a multicopy plasmid reduces the activity of the lac promoter to below 1% of the activity of the unrepressed state). Thus the hok promoter is relatively weak, with an activity of about 50% or less of that of the lac promoter. The sok promoter is about 5 times stronger than the lac promoter and the sok promoter must therefore be at least 10 times more active than the hok promoter.

Induction of the translation of the hok mRNA by the addition of rifampicin

Plasmid pKG780 is a pBR322 derivative carrying the sok gene, the hok'-lacZ hybrid gene derived from pKG733, a part of the lacY gene and the part of the parB region encoding the hok mRNA terminus. Plasmid pKG782 is identical to pKG780 except that the downstream parB insert is replaced by the terminal part of the tetracycline gene derived from pBR322. Despite the high copy number of these plasmids, they express very low levels of β-galactosidase (about one 1 unit in both cases) corresponding to very few β-galactosidase molecules per cell.

Rifampicin was added (300 μg/ml) to exponentially growing cultures of CSH50 containing either pKG780 or pKG782, and samples were withdrawn to determine β-galactosidase activity. There was no increase in activity for the first 10 minutes after the addition of rifampicin, but then an induction of β-galactosidase production (and hence translation of the hok'-lacZ mRNA) was observed. The synthesis of the hok'-lacZ fusion protein lasts for about 80 minutes in both cases. The half-lives of the hok'-lacZ-hok' and the hok'-lacZ-tet' mRNAs were calculated to be about 22 and 20 minutes, respectively (cf. Materials and Methods).

Thus, the insertion of the hok mRNA terminus downstream of the LacZ gene did not cause a significant increase in stability of the hok'-lacZ hybrid mRNA.

Conclusions

Detection of RNA transcripts synthesized from the parB region shows that the hok mRNA initiates at +131/132 and terminates around +562, and that the Sok-RNA initiates at +260 and terminates between +1 and +194. Hence, the Sok-RNA is complementary to the leader sequence of the hok mRNA (FIG. 3). The analysis of promoter and gene fusions between the hok gene and the lacZ gene shows that the sok gene encodes a repressor of hok gene expression acting at a post-transcriptional level. The region from +194 to +336 encodes an active repressor gene, which is transcribed in the opposite direction relative to hok gene transcription. No evident protein coding frame is present in the sok gene region, and it is therefore concluded that the repressor encoded by the sok gene is a small antisense RNA which, by hybridization to the complementary hok mRNA, inhibits the translation of the latter. This observation is supported by the mapping of the target of the sok gene product (sok-T) which was localized to the region encoding the leader sequence of the hok mRNA complementary to the sok-RNA (+194 to +268).

The sok-T region is located upstream of the SD-sequence of the hok mRNA and therefore the repression of translation by the sok rNA by hybridization to the hok mRNA can most likely be explained by its long-range effects (presumably on the secondary structure of the mRNA). The region encoding the leader sequence of the hok mRNA (and hence sok-T) is rich in dyad symmetries. The hok mRNA has the potential to form three stem-loop structures in the region from +194 to +303 shown as 1 ($\Delta G=-16$ kcal/mol), II ($\Delta G=-20$ kcal/mol) and III ($\Delta G=-26$ kcal/mol) in FIG. 3, respectively. The sok mRNA is complementary to the region encoding loop I, part of loop II, but not loop III. The Shine-Dalgarno sequence of the hok gene will, if loop III is formed, be sequestered in the stem of this energy rich loop. It is therefore likely that formation of loop III is a prerequisite of the repression of hok mRNA translation.

The stem-loop structures II and III overlap and therefore cannot be formed simultaneously. If loop II is formed, the SD-sequence would probably not be sequestered in the secondary structure of the mRNA, and the SD-sequence would acquire an "open state" freely accessible to be translated by the ribosomes. It is therefore assumed that hybridization of the sok RNA to the hok mRNA changes the pattern of loop formation of the mRNA from an "open state" (formation of loop II) to a "closed state" (formation of loop III), yielding a mRNA which cannot betranslated by the ribosomes. The β-galactosidase activity expressed from pKG742 in which the hok'-lacZ gene is transcribed from the lacUV5 promoter was unexpectedly low (20 units), as this plasmid does not contain the sok gene. The region upstream of the SD-sequence of pKG742 contains an intact loop III, but not loop I or II. Hence, loop III can be formed persistently, without competition with loop I or loop II, and this could be the reason for the low β-galactosidase expression from this mRNA.

The addition of rifampicin to cells harboring plasmids pKG780 or pKG782 induced synthesis of the hok'-lacZ fusion protein. The hybrid mRNAs were determined to be very stably with a half-life of about 20 minutes. Surprisingly, the hybrid mRNA containing the terminus of the tetracyclin gene mRNA (pKG782) is as stably as the hybrid mRNA which contains the native hok mRNA terminus (pKG780). This result cannot easily be extrapolated to the wild type hok mRNA, but it may be concluded that the 5'-end of the hok mRNA leader sequence (from +1 to +342) encodes a determinant important for the stability of the hok mRNA molecule.

The initial time lag in β-galactosidase synthesis is most readily interpreted as reflecting the time of decay of the inhibitor of hok'-lacZ protein synthesis, i.e. the sok RNA.

The rifampicin-induced time-dependent enhancement of the hybridization reaction between the hok mRNA and the DNA probe used to map the 5'-end of the hok mRNA may most easily be explained as follows: It is known that RNA hybridizes several orders of magnitude faster with RNA than with DNA (Favaloro et al., in *Methods in Enzymology* 65, 1983, pp. 718–749). Therefore, the presence of the sok RNA (before rifampicin addition) inhibits hybridization between the 5'-end of the hok mRNA and the complementary DNA probe because the hok mRNA exhibits a faster hybridization reaction with the sok RNA than with the DNA probe (the sok RNA and the DNA probe used in this experiment are complementary to the same part of the hok mRNA). After addition of rifampicin, which prevents formation of new transcripts, the hybridization between the hok mRNA and the DNA probe complementary to the 5'-end of the hok mRNA greatly increases with time. This enhancement of hybridization reflects the decay of the hybridization inhibitor, the sok RNA. It should be noted that there is no inhibition of hybridization between the hok mRNA and a DNA probe complementary to the 3'-end of the hok mRNA. Considerable amounts of hok mRNA are present in the cells even 25 minutes after the addition of rifampicin indicating that the hok mRNA is extraordinarily stable. These interpretations are in complete agreement with the kinetics of hok'-lacZ fusion protein synthesis observed in the rifampicin induction experiments.

Figure 13:
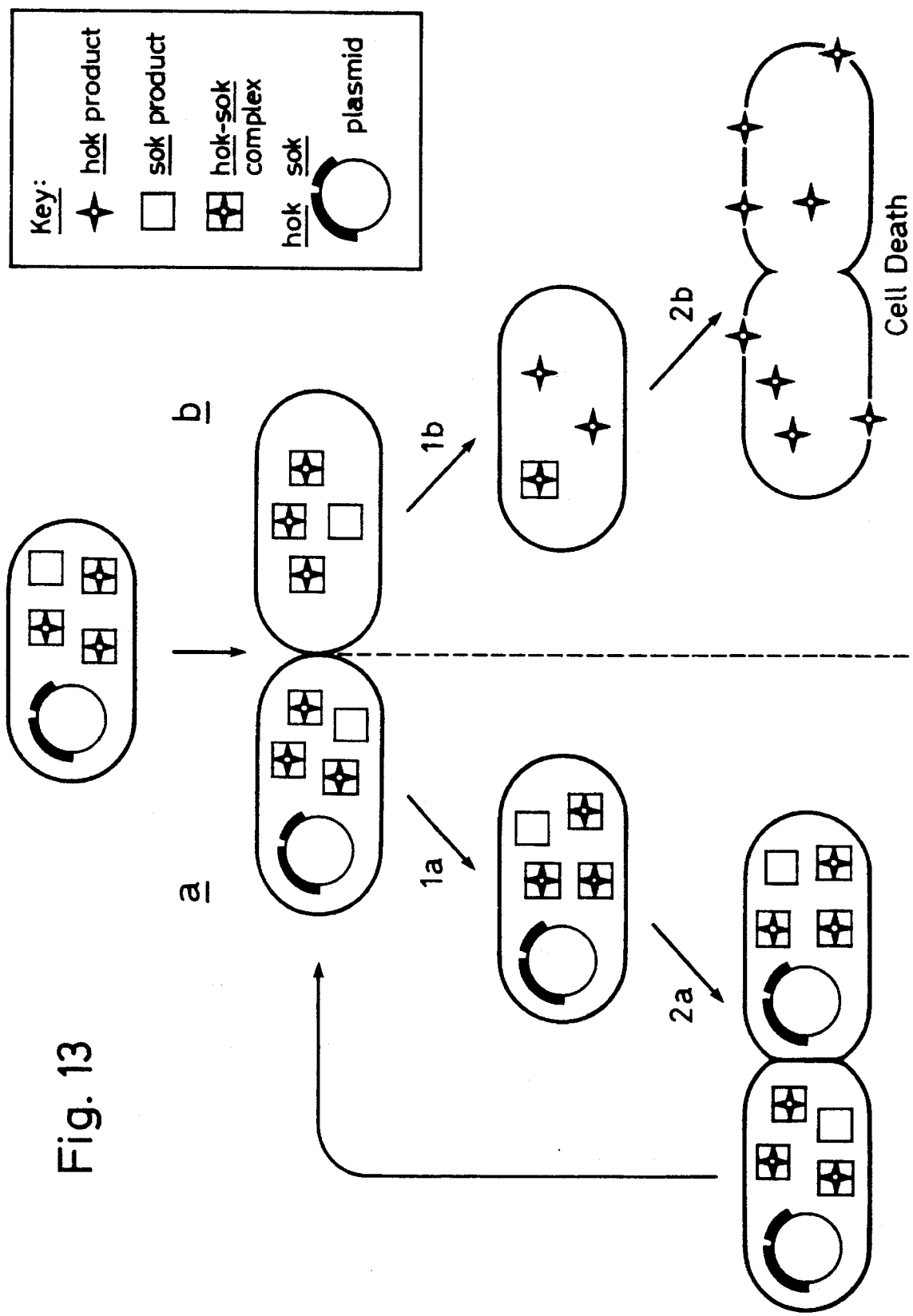
FIG. 13 is a model of the regulation of the hok gene. At cell division, one of the daughter cells receives all the parB+ plasmids present. A. Division cycle of a cell carrying a parB+ (hok+, sok+) plasmid. Both the hok and sok gene products are continuously produced from the plasmid. The sok product antagonizes the hok product and no effect on cell viability is observed (1a+2a). B. Division cycle of a plasmid-free cell. In the plasmid-free cell, the hok and sok products are present. The sok product is degraded faster than the hok product which results in activation of the hok product (1b). This activation results in damage of a vital cell function and cell death (2b).

In FIG. 13, a model explaining the killing of cells which have lost a parB-carrying plasmid during the preceding cell division is presented: The presence of a parB-carrying plasmid in the cell gives rise to cytoplasmic products of the hok and sok genes, the hok mRNA and the Sok RNA. The hok mRNA is stable with a half-life of 20 minutes or more, whereas the Sok RNA which inhibits translation of the hok mRNA is unstable, but present in excess. Hence, in a plasmid-carrying cell, the Sok RNA prevents synthesis of the Hok protein and the cell remains viable. When, on the other hand, a plasmid-free cell appears, e.g. by uneven distribution of the plasmid molecules at cell division, the unstable Sok RNAs decay in this cell leaving the stable hok mRNA freely accessible to be translated by the ribosomes, the Hok protein is synthesized and killing of the plasmid-free cell ensues.

An important testable prediction emerges from the post-segregational derepression model of hok gene expression proposed above:

All unstably inherited plasmids may be stabilized by the parB region, as the killing mechanism is independent of the actual reason for loss of the plasmid. Accordingly, we have shown that the parB region stabilizes many types of replicons, ranging from low copy number plasmids (e.g. R1 (cf. International Patent Application No. PCT/DK83/00086, Publication No. WO84/01172)) to high copy number plasmids (p15A, pBR322, (cf. PCT/DK83/00086, Publication No. WO84/01172) and RSF1010)—all of which have become unstable after genetic manipulation. oriC minichromosomes may also be stabilized by the parB region. Surprisingly, the parB region stabilizes a highly unstable RSF1010 lacZ+ derivative in *P. putida* (cf. Example 12).

Similar regulatory systems involving regulation of the translation of a mRNA species by an antisense RNA molecule have been described previously (Light and Molin, *The EMBO Journal* 2, 1983, pp. 93–98; R. W. Simons and N. Kleckner, *Cell* 34, 1983, pp. 683–691; Mizuno et al., *Proc. Natl. Acad. Sci.*, 1984, 1966–1970), and even artificial systems in which synthetic sequences have been inserted coding for antisense RNA complementary to the leader region of a mRNA have been described (Izant and Weintraub, *Cell* 36, 1984, pp. 1007–1015).

EXAMPLE 6

Figure 8A:
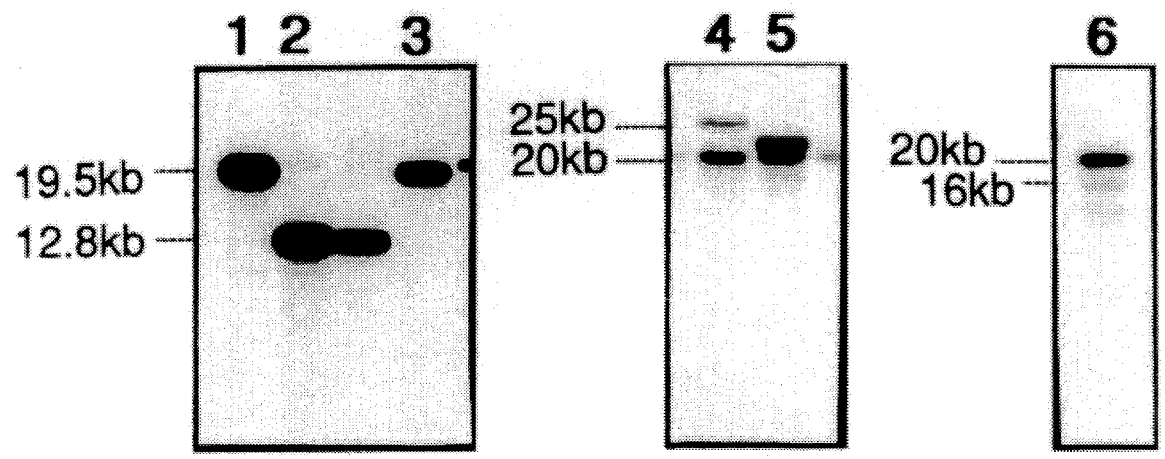
FIG. 8a shows 0.75 µg of EcoRI-restricted total DNA from strains of E. coli analyzed by filter hybridization using the R1 parB probe. Lane 1: R1drd-19; lane 2: R100; lane 3: R386. These lanes were exposed for 30 minutes. Lane 4: RP1; lane 5: R6-K; lane 6: plasmid-free E. coli. These lanes were exposed for 5 hours. Sizes of relevant fragments are given in kilobases.

Discovery of an *E. coli* chromosomal homologue of R1 parB (cf. FIG. 8a)

Since plasmid evolution has involved an extensive exchange of genetic information between bacterial chromosomes and freely replicating DNA molecules, the chromosomal DNA of *E. coli* was analyzed for possible ancestral sequences to the R1 parB sequences.

In lane 6 in FIG. 8a, total EcoRI-restricted DNA from plasmid-free *E. coli* JC411 was analyzed by filter hybridization to a parB probe, cf. Materials and Methods. A fragment of 20 kb is seen to yield a rather weak, but definite signal which can also be detected in other lanes containing *E. coli* DNA if exposed for the same time (lanes 4, 5). The chromosomal sequence is estimated to be approximately 55% homologous to parB. The chromosomal sequence is named par1 in the following.

A major question is of course to which extent the finding of homology at the level of the nucleotide sequence also reflects similarity in function of the products encoded by the homologous regions, an aspect which will be further dealt with in Example 7.

EXAMPLE 7

Genetic organization of an *E. coli* chromosomal homologue of R1 parB and its functional relationship to R1 parB (cf. FIG. 7)

The hok gene of plasmid R1, defined in Example 3, codes for a polypeptide of 52 amino acids. The amino acid sequence of the hok gene product was compared to a large number of known protein sequences. Surprisingly, a polypeptide of 51 amino acids encoded by the relB-orf3 gene of the *E. coli* relB operon (Bach et al., *The EMBO Journal* 4, 1985, pp. 1059–1066) showed significant homology to the hok product. The amino acid sequences of the two homologous proteins are presented in FIG. 7, which shows that 42% (22) of the amino acids are identical in the two proteins. For 17% (9) of the amino acids the changes are conservative, meaning that one amino acid has been replaced with an amino acid of similar chemical characteristics (i.e. hydrophobicity, charge, etc.), resulting in an overall homology of 61%. Especially the charged amino acids are well conserved as are the cysteine residues at positions 16 and 31 (FIG. 7).

The DNA sequences of the hok gene and of relB-orf3 were also compared as shown in FIG. 7. The coordinates used in the following are parB+ sequence coordinates as in FIG. 3. From coordinates +290 to +460, there is 55% homology between the two sequences. It appears from FIG. 7 that the conserved region includes nucleotides upstream and downstream of the protein coding sequence located from +304 to +460. The conservation of bases outside the coding region indicates that regulatory features of the two genes have also been at least partly conserved.

To show that the sequence homology reflects similarity in function a plasmid carrying the λpR promoter fragment upstream of the relB-orf3 gene was constructed (cf. the description of an analogous type of construction used in mapping the hok gene in Example 3).

When λpR mediated transcription into relB-orf3 is induced, a rapid killing of the cells is observed with a kinetics similar to that observed for bacteria containing plasmid pKG341 as described in Example 3. Simultaneously, all the cells in the culture are transformed into the hok characteristic "ghost" cells (cf. FIG. 5).

Thus, there is a striking homology between the hok gene of plasmid R1 and the relB-orf3 of the *E. coli* relB operon both at the structural and functional level.

EXAMPLE 8 parB homologous sequences on various plasmids (cf. FIG. 8a)

Filter hybridization analysis of total, EcoRI-restricted DNA from a number of strains of *E. coli* harbouring various plasmids was carried out using the parB probe (lanes 1–5 in FIG. 8a).

The plasmid R1drd-19 is a member of the R1 plasmid family from which the parB probe was originally cloned. R1drd-19 is present at two copies per bacterial genome. EcoRI-restricted total DNA from *E. coli* 1005/R1drd-19 is analyzed in lane 1. A strongly hybridizing fragment of 19.5 kb is seen, the size of which is consistent with the genetic mapping of the parB function to the 19.5 kb R1 plasmid (International Patent Application No. PCT/DK83/00086, Publication No. WO 84/01172).

The plasmid R100 is closely related to R1 carrying a transposable element, Tn10, within the region equivalent to the 19.5 kb EcoRI-A fragment of R1. The transposon contains the recognition sequence for EcoRI and, consequently, a further EcoRI site is introduced into the R1-like EcoRI-A fragment splitting this into the two EcoRI-A and EcoRI-D fragments of R100 (Miki et al., *J. Bacteriol.* 144, 1980, pp. 87–99). These two EcoRI fragments of R100 both contain sequences found by heteroduplex mapping to be homologous to sequences present of the F factor (Sharp et al., *J. Mol. Biol.* 75, 1973, p. 235). A strongly hybridizing fragment of 12.8 kb is seen in lane 2, FIG. 8a, thereby mapping the parB region of R100 to the EcoRI-D fragment of R100, within the center of the region of homology between R1 and R100, and F.

This localization of parB within the F homology region of R100 prompted the search for parB-like sequences on plasmids belonging to the incompatibility group, IncFI.

EcoRI-restricted, total DNA from B210/R386, an *E. coli* strain harbouring the IncFI plasmid R386, was analyzed by filter hybridization using the parB probe (lane 3, FIG. 8a).

The plasmid R386 which belongs to the same incompatibility group as F was found to give a parB hybridization signal corresponding to an EcoRI fragment of 19.5 kb. Since this plasmid is present at 0.5–1 copies per genome, the finding of a signal of approximately one third of the R100 signal (lane 2, FIG. 8a) suggests that the degree of homology between R1 parB and the R386 parB-like sequences is 55–60%.

The search for parB-related sequences was extended to other incompatibility groups. The plasmid RP1, which belongs to the incompatibility group IncP, was analyzed.

With the parB probe, total, EcoRI-restricted DNA from 1005 (RP1) yields a hybridization signal corresponding to the EcoRI-linearized plasmid (lane 4, FIG. 8a). In addition, a hybridizing band of 20 kb corresponding to par1 is seen, which was discussed in Example 5.

Since RP1 is adapted to stable maintenance in a broad range of gram negative bacterial hosts, the finding of parB-related sequences on RP1 opens the possibility that maintenance systems analogous to the R1 parB system, which is operative in *E. coli* as well as in *Pseudomonas putida* (Example 11), may function in a multitude of bacterial hosts.

Yet another plasmid, R6-K (IncX incompatibility group), was found to carry sequences with approximately the same hybridization characteristics as RP1 as evidenced by the presence of a 25 kb EcoRI fragment of R6-K hybridizing the parB probe (lane 5, FIG. 8a).

The low copy number plasmid F has been analysed in some detail in order to determine whether the presence of R1 parB hybridizing sequences reflect the existence of a stabilization mechanism related to that of R1 parB.

Two plasmid stabilization functions have been identified within the genome of F and the corresponding genes (sop (Ogura and Hiraga, *Cell* 32, 1983, pp. 351–360) and ccd (Ogura and Hiraga, *Proc. Natl. Acad. Sci. USA* 80, 1983, pp. 4784–4788)) have been located to the EcoRI fragment spanning the map positions 40.3 to 49.5.

Filter hybridization analysis of total DNA from *E. coli* 1005 harbouring F showed that R1 parB-related sequences were present on a 10.7 kb EcoRI fragment of F (map position 49.5 to 60.2) and further hybridization analyses of 1005(F) DNA digested with EcoRI and/or BamHI mapped these sequences to a 4.5 kb BamHI-EcoRI fragment extending from map position 55.7 to 60.2. This indicates the existence of a third plasmid stabilizing function within F.

The region of F hybridizing the R1 parB probe was subsequently cloned into a bacteriophage λ vector. EcoRI-digested DNA from 1005(F) was size-fractionated by preparative agarose gel electrophoresis and fragments of 9.5 to 12 kb were recovered by electroelution from the gel. The fragments were ligated to the EcoRI sites of the left and right arms of λL147 and packaged in vitro to yield infectious phages (cf. Maniatis et al., *Molecular Cloning*, Cold Spring Harbor, N.Y., 1982, p. 256) which were then used to infect *E. coli* LE392. Recombinant phages carrying the R1 parB related sequences were identified by plaque hybridization.

From a recombinant phage carrying the 10.7 kb EcoRI fragment which includes the R1 parB related sequences, the fragment was isolated and inserted into pUC8 at the EcoRI site. In one resulting plasmid, pNL1, the insert is so oriented that cleavage of pNL1 DNA with BamHI results in excision of a 4.5 kb fragment carrying the R1 parB hybridizing sequences.

The 4.5 kb BamHI fragment from pNL1 was isolated and the region hybridizing the R1 parB probe was mapped to an RsaI fragment of 870 bp by filter hybridization analysis. The 870 bp RsaI fragment was isolated and inserted into the SmaI site of M13mp9. A number of recombinant phages carrying the R1 parB related sequences on a 870 bp insert was identified by plaque hybridization. The nucleotide sequence of the inserted DNA was analysed according to Sanger et al., *Proc. Natl. Aced. Sci. USA* 74, pp. 5463–5467 (1977).

The nucleotide sequence of part of one of the recombinant phages, mpNL12, comprises 402 bases extending from the RsaI site and this sequence is 90% homologous to the region from +178 to +580 of the R1 parB sequence (FIG. 3). All essential features of the R1 parB region are also found in the F-derived sequence: (1) an open reading frame encoding a protein of 50 amino acids is present corresponding to the R1 hok gene, (2) the ribosome binding site of R1 hok is conserved, (3) the region corresponding to the 3' non-translated part of R1 parB mRNA, which is believed to be essential for hok mRNA stability, is highly conserved (90% homology), and (4) the putative −10 and −35 regions of R1 sok are also conserved.

The open reading frame within the F-derived sequence codes for a protein of 50 amino acids which differs only slightly from the R1-specified hok protein. Firstly, two codons in R1 hok have been deleted, namely val-15 and ser-29. Secondly, two conservative substitutions have occurred, namely leu-16 to val and his-39 to tyr.

Evidently, the R1 hok gene and the related sequences on F derive from a common ancestral sequence and, furthermore, the conservation of a coding region corresponding to R1 hok strongly suggests that the encoded protein is involved in the stabilization of F.

To test for plasmid stabilizing properties of the F-derived sequence, the 4,5 kb BamHI fragment from pNL1 which carries the F hok-like sequences was inserted into pJEL82, a low copy number plasmid with a loss frequency of $10^{-2}$ per generation (cf. PCT/DK83/00084, Publication No. WO84/01171). The resulting plasmid, pJEL82/F, as well as pJEL82 was transformed into *E. coli* HB101. Cultures of the two strains were grown for 16 hours without selection pressure and the fraction of plasmid-containing cells ($Ap^R$) was determined. The result was as follows:

| plasmid | % $Ap^R$ cells |
| --- | --- |
| pJEL82 | 36.5 |
| pJEL82/F | 98.4 |

It was therefore concluded that the 4.5 kb BamHI fragment carrying R1 parB related sequences exerts a plasmid stabilizing effect. If the stabilization is due to the presence of the hok-like gene within the F fragment, the emergence of ghost cells would be expected in cultures of cells harbouring pJEL82/F grown without selection pressure, cf. Example 3. An overnight culture of cells containing pJEL82/F was found to contain approx. 5% ghost cells indistinguishable from R1 hok induced ghost cells.

In case of F, the demonstration of sequences related to R1 parB by filter hybridization thus reflects the existence of a functionally similar plasmid stabilization mechanism.

EXAMPLE 9

Figure 8B:
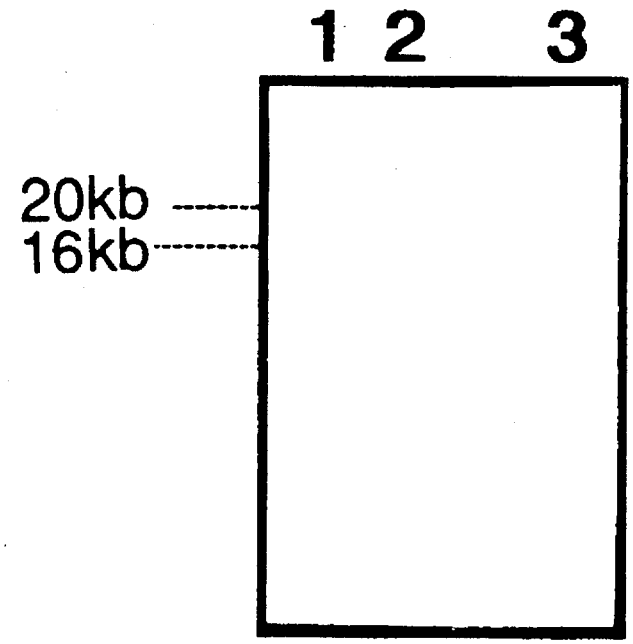
FIG. 8b shows 0.75 µg of EcoRI-restricted total DNA from strains of E. coli analyzed by filter hybridization using the relB-orf3 probe. Lane 1: R100; lane 2: R386; lane 3: plasmid-free E. coli. Time of exposure: 3.5 hours. Sizes of relevant fragments are given in kilobases.

Stepwise hybridization as a strategy for the detection of replicon stabilizing sequences homologous to parB related sequences (cf. FIG. 8b)

The conditions of hybridization determine the level of homology between a probe and a filter-bound DNA species required to yield a detectable signal, cf. the discussion in Materials and Methods. Consequently, filter-bound sequences may exist which remain undetectable with the given probe under the given set of hybridization conditions but which may nevertheless encode a hok-like activity, cf. the discussion of homology versus function in Materials and Methods. This is illustrated in the following experiment.

As described in Example 6, the relB-orf3 represents a chromosomal homologue of R1 parB based on the sequence comparison data and the functional similarity of hok and relB-orf3. The relB-orf3 and flanking sequences, as present in plasmid pBD2724, was used as probe in a filter hybridization analysis of E. coli chromosomal DNA.

Plasmid pBD2724 is a pBR322 derivative containing a HincII-MluI fragment from the relB operon of E. coli comprising the relB-orf3 coding sequence (coordinates 1070–1350 according to Bech et al., op. cit.).

In lane 3, FIG. 8b, total EcoRI-restricted DNA from plasmid-free E. coli is analyzed by filter hybridization using the relB-orf3 probe. In addition to the 20 kb hybridizing fragment likely to represent the above-identified parI sequence (Example 6), yet another hybridizing fragment of 16 kb is detected. Since the intensity of the latter is greater than the intensity of the 20 kb signal, the 16 kb EcoRI fragment must span the E. coli relB-orf3 gene used as hybridization probe, i.e. the intensity of the 16 kb signal provides a reference from which degrees of homology can be estimated. The intensity of the parI hybridization signal, which is approximately ¾ of the relB-orf3 signal, suggests that parI is approximately 65–70% homologous to relB-orf3. Since the 16 kb relB-orf3-carrying fragment is not detected with the parB probe (lane 6, FIG. 8a), R1 parB is 50% or less homologous to relB-orf3.

In Example 5 it was found that the parB probe detects the 20 kb chromosomal homologue but not the 16 kb homologue representing according to the above data the relB-orf3. Since, as described in Example 6, the latter exerts hok-like activity when expressed, it can be assumed that the parI will also express hok-like activity or sok-like activity and/or both activities when properly expressed.

The relB-orf3 fragment was used as a probe in filter hybridization analysis of E. coli harbouring plasmid R100 and R386, both of which contain R1 parB-like sequences (FIG. 8a, lanes 2 and 3). Under the present set of hybridization conditions, the relB-orf3 probe did not detect these sequences (FIG. 8b, lanes 1 and 2) since only the 20 kb par'1 and the 16 kb relB-orf3 carrying fragment are seen to hybridize the probe, thereby indicating that the absence of hybridization between a probe from a region expressing hok or hok-like activity and a given DNA-species does not preclude that the DNA-species in question can exert hok-like activity if properly expressed. Consequently, the finding of homology between the DNA-species in question and a region expressing hok or hok-like activity strongly suggests that the DNA-species in question will exert hok or hok-like activity if properly expressed.

The above data therefore reveal a useful strategy in searching for regions exerting hok/sok-like activities: A probe representing a region of nucleic acid comprising hok or hok-like genes (e.g. R1 parB) is used to detect homologous sequences (e.g. par1) within the genome in question (e.g. chromosomal or plasmid DNA) which are subsequently tested for hok or hok-like activity (as done for the relB-orf3 region) in the proper experimental settings, and if shown to encode such activity or activities are next used themselves as probes in a second round of hybridizations to define novel homologous sequences which may or may not be related to the probes used in the first round of hybridizations (e.g. R1 parB). This stepwise procedure combining nucleic acid hybridization and functional assays of the isolated nucleic acid sequences may be adapted as a general strategy to search for genes expressing hok or hok-like activities in genomes increasingly separated from E. coli on the evolutionary scale.

EXAMPLE 10

Figure 9A:
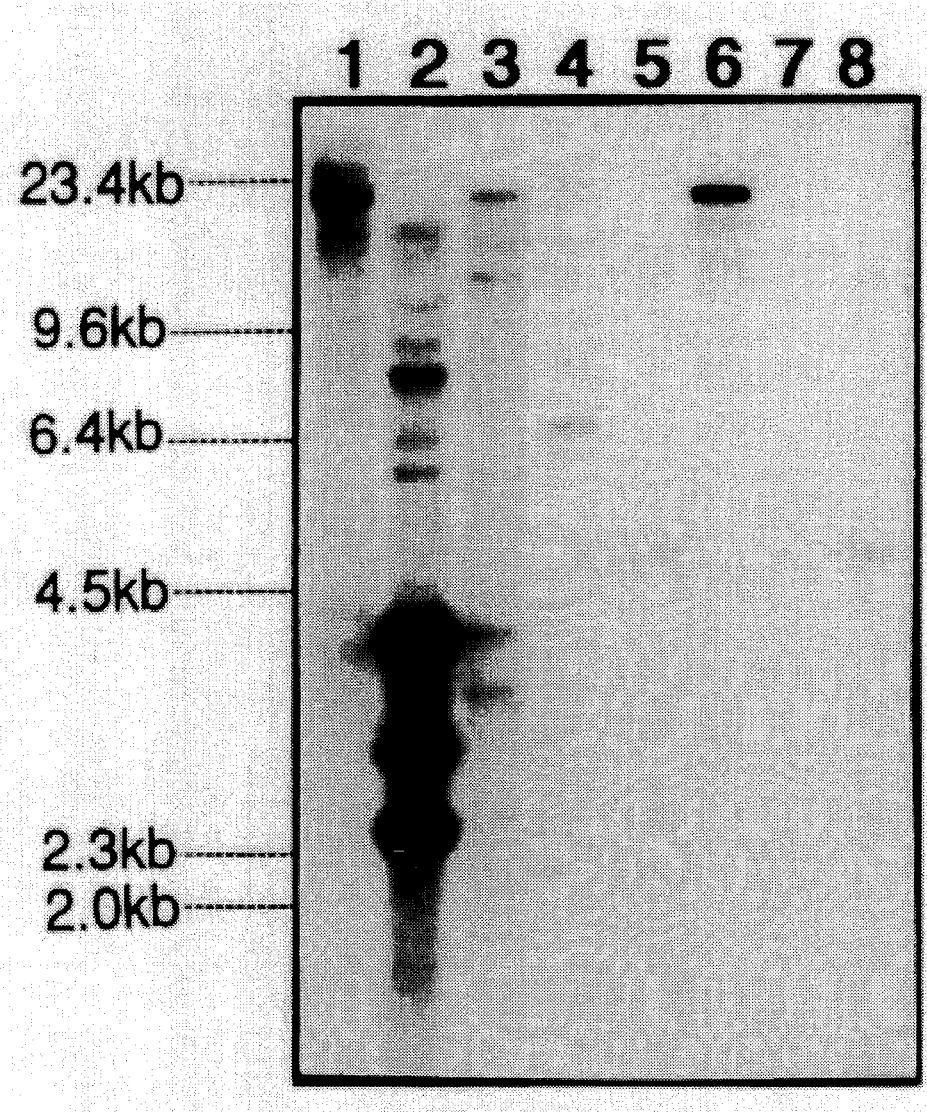
FIGS. 9A and 9B show 0.5–0.75 µg of EcoRI-restricted total DNA from various bacteria analyzed by filter hybridization using the R1 parB probe. The autoradiogram was exposed for 17 hours. Two different photographic exposures of the same autoradiogram are shown. Lane 1: *Salmonella typhimurium* (not discussed in the text); lane 2: *Serratia marcescens*; lane 3: *Pseudomonas fluorescens*; lane 4: *Pseudomonas putida*; lane 5: *Proteus vulgaris* (not discussed in the text); lane 6: *Escherichia coli*; lane 7: *Bacillus subtilis*; lane 8: *Bacillus circulans* PL236. Sizes of radioactively labelled marker (λ restricted with HindIII) are given in kilobases.
Figure 9B:
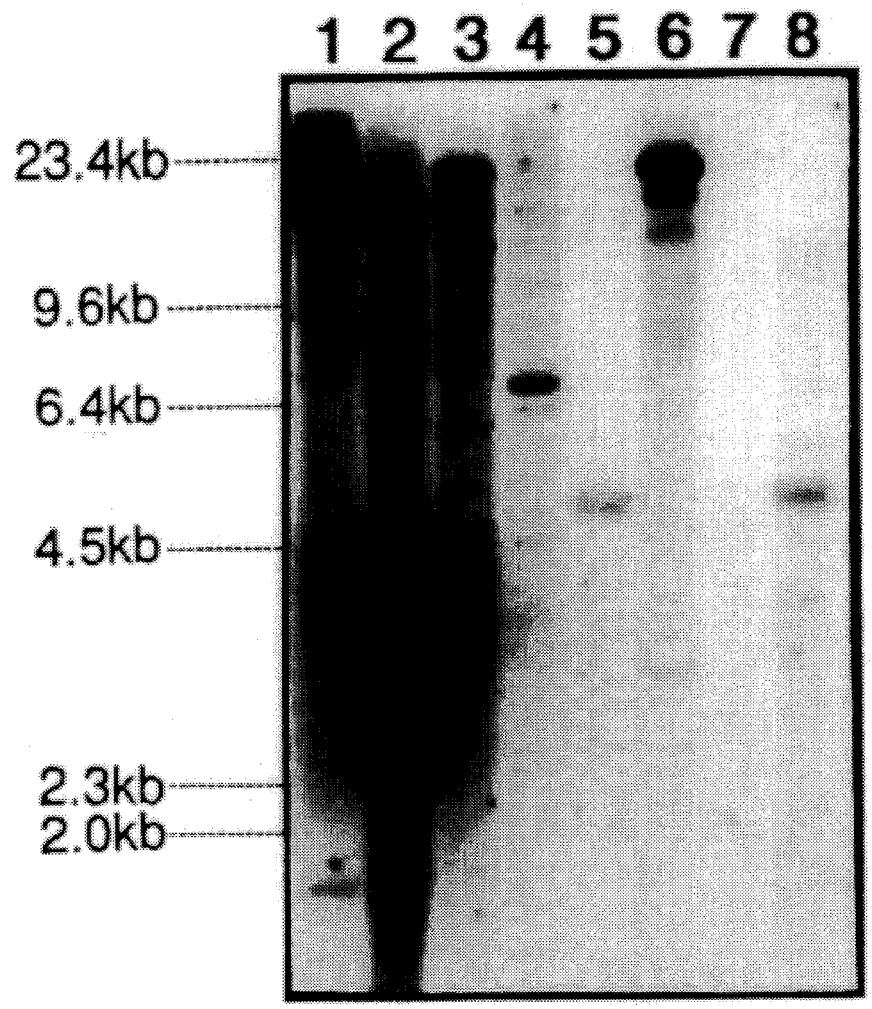
Figure 10:
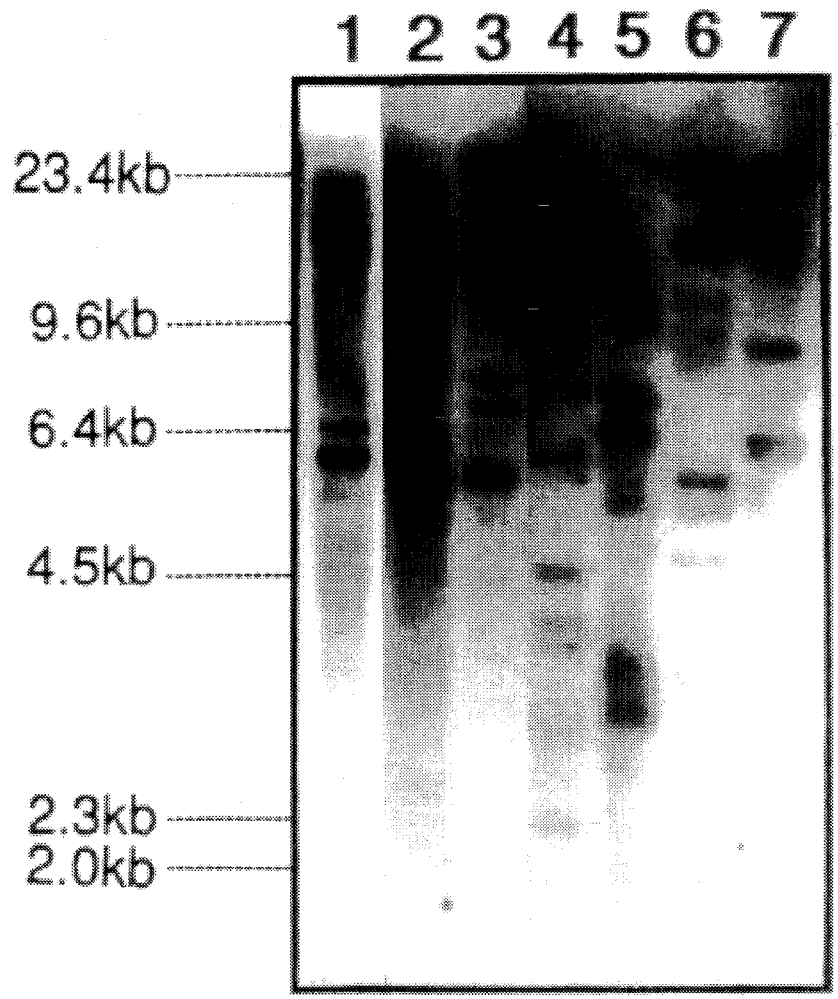
FIG. 10 shows 0.5–0.75 µg of EcoRI-restricted total DNA from various bacteria analyzed by filter hybridization using the relB-orf3 probe. The autoradiogram was exposed for 17 hours (lane 1) and 72 hours (lanes 2–7). Lane 1: *Serratia marcescens*; lane 2: *Pseudomonas fluorescens*; lane 3: *Pseudomonas putida*; lane 4: *Bacillus subtilis*; lane 5: *Bacillus circulans* PL236; lanes 6, 7: Lactobacillus. Sizes of radioactively labelled marker (λ restricted with HindIII) are given in kilobases.

Detection of parB related sequences in bacteria (cf. FIGS. 9 and 10)

In the previous Examples, it was demonstrated 1) that sequences related to R1 parB are widely distributed among bacterial plasmids isolated from gram-negative bacteria, and 2) that sequences related to R1 parB are present in the chromosomal DNA of E. coli. These findings prompted a search for sequences related to either R1 parB or one of the chromosomal counterparts (E. coli relB-orf3) in DNA from a variety of bacteria, as part of either their chromosomal DNA or of plasmids naturally present in these organisms.

Filter hybridization analysis of EcoRI-restricted DNA from Serratia marcescens with the R1 parB probe shows intense hybridization to 3 fragments of 4.1, 2.9 and 2.5 kb (lane 2, FIG. 9). Only the 4.1 kb fragment also hybridizes the relB-orf3 probe (lane 1, FIG. 10). The parB probe hybridizes an additional 6 fragments. Two of these signals are stronger than the parB signal derived from the relB-orf3-carrying 16 kb fragment in E. coli DNA (lane 6, FIG. 9). Hybridization of Serratia marcescens DNA with the E. coli relB-orf3 probe yields a number of weak hybridization signals. It is possible that the strongly hybridizing bands of 2.5, 2.9 and 4.1 kb are derived from plasmid(s) although the agarose gel electrophoresis did not reveal any high copy number plasmids.

Pseudomonas fluorescens was analyzed as a plasmid-free member of this species. Hybridization of DNA from Pseudomonas fluorescens with R1 parB (lane 3, FIG. 9) shows 8–10 hybridizing fragments, 4 of which exhibit signals with intensities of approximately 33% of the chromosomal counterpart of R1 parB (lane 6, FIG. 9). A single of these fragments, of approximately 13 kb, probably also hybridizes the E. coli relB-orf3 probe (lane 2, FIG. 10). In addition, the relB-orf3 probe identifies 5 fragments specifically, although at low signal intensity; two of these, of 5.5 and 5.6 kb, are also seen in DNA from Pseudomonas putida when this DNA is analyzed using the relB-orf3 probe (lane 3, FIG. 10). The relB-orf3 probe hybridizes to an additional 5 fragments in Pseudomonas putida DNA, but none of these fragments are recognized by the R1 parB probe (lane 4, FIG.

9). In *Pseudomonas putida* DNA, the parB probe detects approximately 10 fragments of low signal intensity and a single quite strongly hybridizing fragment of approximately 7.3 kb.

Among grampositive bacteria, *B. subtilis, B. circulans* PL236 and two strains of Lactobacillus were analyzed for the presence of sequences related to either R1 parB or *E. coli* relB-orf3.

In case of the parB probe, a single quite strongly hybridizing fragment of 5.2 kb was found in DNA from *B. circulans* (lane 8, FIG. 9). Very weak signals were obtained from a few additional fragments of *B. circulans* DNA. With the relB-orf3 probe, a limited number of hybridizing fragments was seen in DNA from *B. subtilis* (lane 4, FIG. 10), *B. circulans* (lane 5, FIG. 10), and Lactobacillus (lanes 6 and 7, FIG. 10). The number of relB-orf3-hybridizing fragments ranged from 6 to 11, and all have approximately the same signal intensity. In the Lactobacilli, agarose gel electrophoresis has demonstrated the presence of plasmids suggesting the possibility that at least some of the hybridizing sequences are of plasmid origin. A search for plasmids in *B. circulans* PL 236 has been negative suggesting that the sequence of *B. circulans* DNA hybridizing the R1 parB probe (lane 8, FIG. 9) may be of chromosomal origin.

The above experiments indicate that sequences related to R1 parB and/or to *E. coli* relB-orf3 are widely distributed among bacterial species, not only the Enterobacteriaceae from which the probes were derived, but also the grampositive bacteria.

EXAMPLE 11

Figure 11:
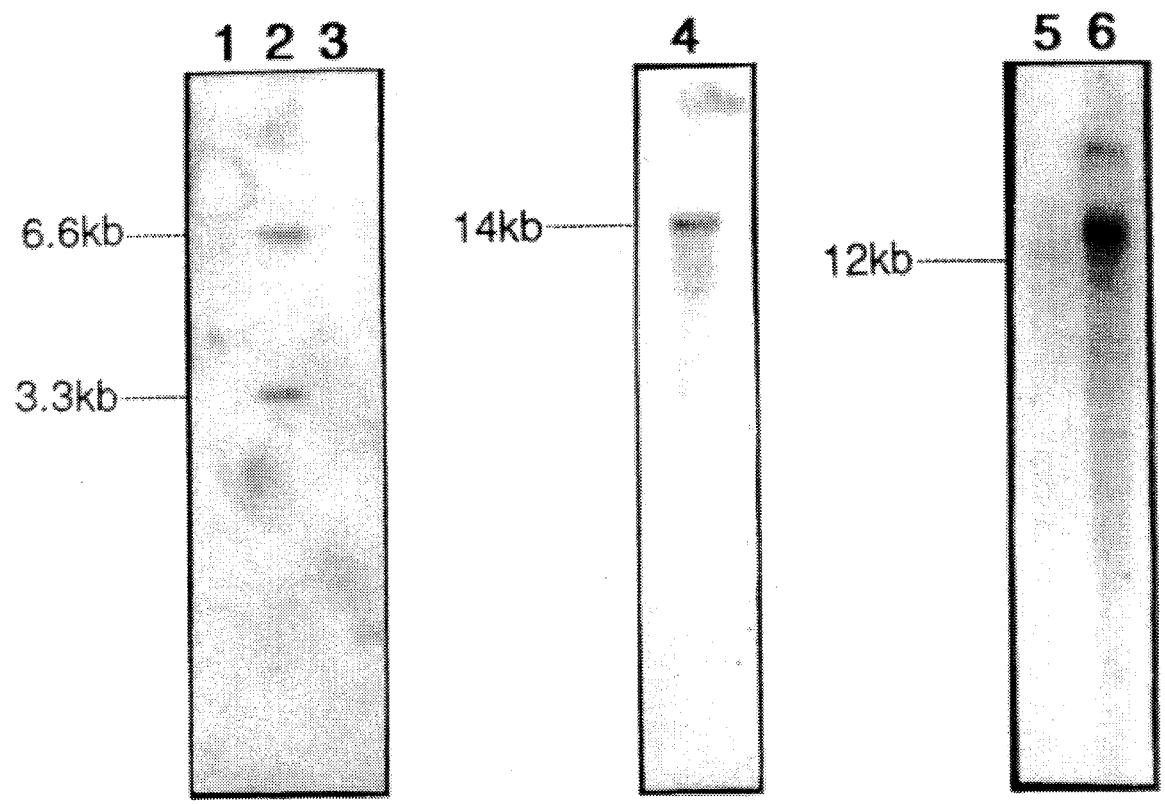
FIG. 11 shows filter hybridization analyses of DNA from eukaryotic cells using the relB-orf3 probe (lanes 1–4) as well as the R1 parB probe (lanes 5–6). The DNA was cleaved with EcoRI (lanes 1–3 and 5–6) or with PstI (lane 4). Lane 1: 5 µg of macronuclear DNA from *Tetrahymena thermophila*; lane 2: 5 µg of total DNA from *Tetrahymena thermophila*; lane 3: 5 mg of rDNA from *Tetrahymena thermophila*; lane 4: 0.25 µg of chloroplast DNA from *Pisum sativum*; lane 5: 5 µg of total cellular DNA from neuroblastoma; lane 6: 10 µg of total cellular DNA from embryonic liver. Sizes of fragments are given in kilobases.

Detection of parB related sequences in eukaryotic cells (cf. FIG. 11)

A unicellular eukaryotic organism was investigated, namely the ciliate protozoan *Tetrahymena thermophila*, FIG. 11. This organism is characterized by 1) a high number of mitochondrial DNA molecules per cell and 2) approximately 12,000 copies of ribosomal RNA genes located on self-replicating rDNA molecules. Neither the R1 parB probe nor the *E. coli* relB-orf3 probe detect any fragments in DNA prepared from isolated macronuclei (lane 1, FIG. 11). Nor did the probes hybridize to the two EcoRI fragments of isolated rDNA (lane 3, FIG. 11). Total EcoRI-restricted DNA from *Tetrahymena thermophila*, which includes mitochondrial DNA, showed two hybridizing fragments, of 6.6 kb and 3.3 kb (lane 2, FIG. 11), with the relB-orf3 probe while the parB probe did not yield any signals. The hybridizing fragments co-migrated with two EcoRI fragments of mitochondrial DNA that were readily detectable by ethidium bromide staining of the gel prior to DNA transfer.

Chloroplast DNA from pea (*Pisum sativum*) was cleaved with the restriction endonuclease PstI and 0.125 μg was analyzed by filter hybridization using the parB and the relB-orf3 probes (lane 4, FIG. 11). The latter probe hybridizes to a fragment of approximately 16 kb.

Finally, two samples of human cellular DNA were analyzed by filter hybridization following EcoRI restriction. The R1 parB probe yielded a (weak) hybridization signal to the neuroblastoma DNA (lane 5, FIG. 11) as well as to the embryonic liver DNA (lane 6, FIG. 11). The high mitochondrial content of liver tissue may indicate that the observed signal in lane 6, FIG. 11, is derived from human mitochondria.

The neuroblastoma DNA was analyzed since other hybridization analyses had indicated selective amplification of a small chromosomal region leading to the presence of extrachromosomal mini-chromosomes ("double minutes"); the origin of the hybridization signal in lane 5, FIG. 11, is unknown.

EXAMPLE 12

Figure 12:
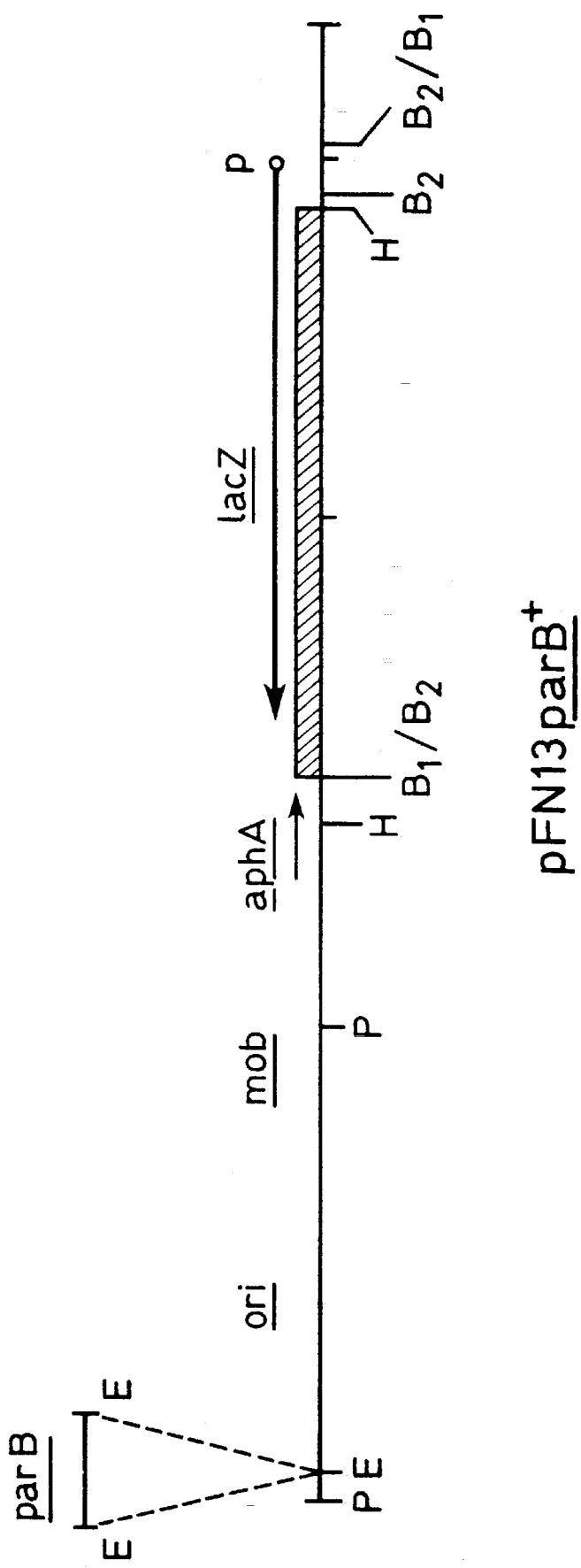
FIG. 12 shows a map of the broad host range plasmid pFN13 parB+. ori denotes the origin of replication; mob denotes a sequence which enables the plasmid to be transferred by conjugation to most other gram negative species when a conjugative (i.e. mobilizing) plasmid is present in the same cell; aphA represents a gene conferring kanamycin resistance; lacZ is the gene encoding β-galactosidase; p symbolizes the repA promoter from plasmid R1; parB represents the R1 derived plasmid maintenance function encoding the hok and sok genes. Restriction sites are shown as P (PstI), E (EcoRI), H (HindIII), $B_1$ (BamHI) and $B_2$ (BglII).

Complete stabilization of highly unstable recombinant plasmids in *P. putida* and *S. marcescens* by the parB region (cf. FIG. 12)

When cloning foreign DNA into *Pseudomonas spp.*, it has been observed that the introduced plasmids often become highly unstable. This plasmid instability was postulated to be caused by induction of an unknown host cell function, which in some way recognizes and eliminates the foreign DNA (Kim and Meyer, *J. Bacteriol.* 159, 1984, pp. 678–682). As *Pseudomonas spp.* are highly relevant for industrial purposes, it was considered to be important to test the effect of parB on such highly unstable recombinant plasmid derivatives.

Plasmid pKT230 is a cointegrate plasmid consisting of the broad host range vector RSF1010 (capable of being stably maintained in a wide range of gram negative bacteria) and pACYC177, a derivative of the natural p15 plasmid (Bagdasarian et al. *Gene* 16, 1981, pp. 237–242). A BglII restriction fragment of plasmid pJL217 (Light and Molin, *Mol. Gen. Genet.* 187, 1982, pp. 486–493), which contains the lac genes, was inserted into the unique BamHI restriction site of pKT230, resulting in pFN13. Plasmid pFN13, which has a high copy number, is stably maintained in *E. coli*, with a loss frequency of less than $10^{-4}$ per cell per generation. In *P. putida*, however, the same plasmid derivative has a loss frequency of 30% per cell per generation. In *S. marcescens* the loss frequency is 5% per cell per generation.

To test the effect of parB, the parB EcoRI fragment of pPR95 was inserted into the unique EcoRI site of pFN13. The resulting plasmid was designated pFN13 parB$^+$, a map of which is presented in FIG. 12.

Plasmid pFN13 was mobilized by a conjugative plasmid into *P. putida* and *S. marcescens*, selecting for kanamycin resistance in both cases. The loss frequency of pFN13 parB$^+$ in both *P. putida* and *S. marcescens* was less than $10^{-6}$ per cell per generation, corresponding to an increase in plasmid stability in *P. putida* of at least $10^5$ fold, and in *S. marcescens* of at least $10^4$ fold.

Thus, it can be concluded that the parB$^+$ region is very efficient in securing the stability of highly unstable recombinant plasmids even in bacterial species distantly related to *E. coli*.

EXAMPLE 13

To analyze if the R1 hok gene exerts a cell killing effect in gram-positive bacteria, e.g. *Bacillus subtilis*, if properly expressed from a *B. subtilis* promoter, the parB region is isolated from pPR95 (FIG. 2) as an EcoRI fragment. The EcoRI sites are filled in using Klenow polymerase in order to generate blunt ends, and the fragment is subsequently digested with FspI. The 300 bp FspI-(EcoRI) fragment (spanning the map position +286 to +580 in FIG. 3) lacking the hok promoter is isolated and inserted into pSI-1 (Yansura & Henner, *Proc. Natl. Acad. Sci. USA* 81, 1984, p. 439) which has been digested with SalI and subsequently treated with mung bean nuclease (Rosenberg et al., *Meth. Enzymol.* 101, 1983, p. 123) in order to remove the 5' single stranded overhanging ends. The ligation mixture is transformed to *E. coli* MC1000 (Casabadan & Cohen, *J. Molec. Biol.* 138, 1980, pp. 179–207).

This construction positions the hok gene, including the hok ribosomal binding site, close to a synthetic *B. subtilis* ribosomal binding site present on pSI-1, a *B. subtilis - E. coli* shuttle vector. The expression of the inserted gene is governed by the SPO1 promoter on pSI-1, the activity of which is regulated via the lac operator present between the promoter and the synthetic ribosomal binding site (spac-I promoter, Yansura & Henner, op.cit.). The pSI-1 furthermore expresses the lacI gene which codes for the lac repressor. *E. coli* transformants are analyzed for IPTG (isopropylthio galactoside) induced growth inhibition as the SPO1 promoter is active in *E. coli*. The screening is performed by replica plating from plates containing 8 μg/ml of chloramphenicol to plates containing chloramphenicol and IPTG (1 mM). Colonies that grow poorly in the presence of IPTG are further analyzed in liquid culture to confirm the phenotype. A number of transformants showing formation of ghost cells (cf. Example 3) when IPTG is added to 1 mM, are identified.

Transformants are furthermore grown in liquid culture to $OD_{600}=0.2$ at which point IPTG is added to 1 mM. Addition of IPTG results in growth arrest and formation of ghost cells (cf. Example 3) in the culture.

Plasmid DNA is isolated from such IPTG-sensitive *E. coli* transformants and introduced into *B. subtilis* BD224 by protoplast transformation (Chang & Cohen, *Molec. gen. Genet*, 168. 1979, p. 111) with subsequent selection for chloramphenicol resistant transformants.

To analyze for a possible cell killing effect of R1 hok in *B. subtilis*, the $Cm^R$ resistant *B. subtilis* transformants are plated in the absence or presence of 1 mM of IPTG. If no growth or severe growth inhibition is observed in the presence of IPTG, the R1 hok is properly expressed. It is then possible to impose a sok-like antisense RNA regulation on the translation of the hok mRNA by appropriate constructions as indicated above.

We claim:

1. A living bacterial cell of a gram-negative bacterial species other than *E. coli,* said cell harbouring a recombinant replicon capable of replicating in said cell which comprises:
   (a) a first mRNA-encoding DNA sequence which comprises a peptide coding sequence which has essentially the same sequence and function as the peptide coding sequence of the R1 par hok gene as set forth in FIG. 3 or the relB-orf3 gene of the *E. coli* operon as set forth in FIG. 7, in any case operably linked to a first promoter functional in said cell so as to control transcription of a first RNA molecule which codes for a first peptide product capable of killing the cell or its progeny; and
   (b) a second mRNA-encoding DNA sequence which has essentially the same sequence and function as the coding sequence of the R1 parB sok gene as set forth in FIG. 3, operably linked to a second promoter functional in said cell so as to control transcription of a second RNA molecule which inhibits the translation of the first mRNA molecule in cells harbouring the replicon,
   whereby the inhibiting RNA molecule decays and the inhibiting molecule is no longer expressed when the replicon is lost from the cell, whereby translation of the killing product present in the new replicon-free cell is no longer suppressed by the inhibiting molecule, resulting in cell death,
   wherein at least one of said first and second DNA sequences is operably linked to a promoter with which it is not natively associated or joined directly to flanking DNA with which it is not natively associated.

2. The cell of claim 1, wherein upon propagation of said cell, said replicon is inherited over at least 100 cell generations with a loss of less than $10^{-4}$/cell/generation.

3. The cell of claim 1, the cell being of a Pseudomonas species.

4. The cell of claim 3, wherein the cell is Pseudomonas putida.

5. The cell of claim 1, wherein the cell is of a Serratia species.

6. The cell of claim 5, wherein the cell is a *Serratia marcescens*.

7. The cell of claim 1, wherein said replicon has a loss frequency in said cell which is reduced by a factor of at least $10^4$ as compared to the loss frequency in said cell of said replicon in the absence of genetic elements (a) and (b).

8. The cell of claim 1, wherein the replicon is a plasmid with a copy number averaging no more than 2 copies per cell.

9. The cell of claim 1, wherein the replicon is stabilized independent of any external selection pressure.

10. A process for producing a gene product which comprises cultivating a gram-negative bacterial cell other than an *E. coli* cell according to claim 1, the recombinant replicon of said cell further comprising a third gene encoding said gene product and a promoter functional in said cell and operably linked to said third gene, under conditions conducive to expression of said third gene.

11. A process for making a stabilized gram-negative bacterial cell other than an *E. coli* cell which comprises (I) inserting into a replicon which replicates in said cell one or more inserts which collectively include
   (a) a first mRNA-encoding DNA sequence which comprises a peptide coding sequence having essentially the same nucleotide sequence and function as the coding sequence of the R1 parB hok gene set forth in FIG. 3 or the relB-orf3 gene set forth in FIG. 7, in any case operably linked to a first promoter functional in said cell so as to control transcription of a first mRNA molecule coding for a first peptide product capable of killing the cell or its progeny, and
   (b) a second mRNA-encoding DNA sequence having essentially the same nucleotide sequence and function as the coding sequence of the R1 parB sok as set forth in FIG. 3, in either case operably linked to a second promoter functional in said cell so as to control transcription of a second RNA molecule which inhibits the translation of the first mRNA molecule in cells harbouring the replicon,
   whereby the inhibiting RNA molecule decays and the inhibiting molecule is no longer expressed when the replicon is lost from the cell, whereby translation Of the killing product present in the new replicon-free cell is no longer suppressed by the inhibiting molecule, resulting in cell death,
   and (II) transforming a bacterial cell with the resulting recombinant replicon to obtain a stabilized bacterial cell.

12. A living bacterial cell of a gram-negative bacterial species other than *E. coli,* said cell harbouring a recombinant replicon capable of replicating in said cell which comprises:
   (a) a first mRNA-encoding DNA sequence which comprises a peptide coding sequence which is essentially the same nucleotide sequence as the coding sequence of the R1 par hok gene as set forth in FIG. 3 or the relB-orf3 gene set forth in FIG. 7, in any case operably linked to a first promoter functional in said cell so as to control transcription of a first RNA molecule which codes for a first peptide product capable of killing the cell or its progeny; and (b) a second mRNA-encoding DNA sequence which is essentially the same nucleotide sequence as the R1 parB sok sequence set forth in FIG. 3, operably linked to a second promoter functional in said cell so as to control transcription of a second RNA molecule which inhibits the translation of the first mRNA molecule in cells harbouring the replicon, whereby the inhibiting RNA molecule decays and inhibiting molecule is no longer expressed when the replicon is lost from the cell, whereby translation of the killing product present in the new replicon-free cell is not longer suppressed by the inhibiting molecule, resulting in cell death, where at least one of said first and second DNA sequences is not identical to the corresponding R1 parB hok or sok gene mRNA-encoding sequence as set forth in FIG. 3.

13. The cell of claim 12 where the first sequence is not identical to the R1 parB hok mRNA-encoding sequence and the second sequence is not identical to the R1 parB sok mRNA-encoding sequence.

14. The cell of claim 12 wherein said first product capable of killing the cell or its progeny is not identical to the killing product encoded by R1 parB hok.

* * * * *